United States Patent
Sekiguchi et al.

(10) Patent No.: US 10,251,548 B2
(45) Date of Patent: Apr. 9, 2019

(54) IMAGE PROCESSING APPARATUS, ESTIMATION METHOD, SYSTEM, AND MEDIUM

(71) Applicant: CANON KABUSHIKI KAISHA, Tokyo (JP)

(72) Inventors: Hiroyuki Sekiguchi, Kyoto (JP); Akihito Uji, Kyoto (JP); Daisuke Kawase, Ichikawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 44 days.

(21) Appl. No.: 15/405,197

(22) Filed: Jan. 12, 2017

(65) Prior Publication Data

US 2017/0202453 A1    Jul. 20, 2017

(51) Int. Cl.
*A61B 3/10* (2006.01)
*G06T 7/564* (2017.01)
(Continued)

(52) U.S. Cl.
CPC ............ *A61B 3/102* (2013.01); *G06T 7/0012* (2013.01); *G06T 7/11* (2017.01); *G06T 7/564* (2017.01);
(Continued)

(58) Field of Classification Search
CPC ......... G06T 2207/30041; G06T 7/0012; G06T 2207/10101; G06T 7/162; G06T 7/11; G06T 2207/10004; G06T 2207/10076; G06T 2207/10081; G06T 2207/20161; G06T 2207/30048; G06T 2207/30101; G06T 7/12; G06T 11/005; G06T 11/003; G06T 2207/20116; G06T 7/564; G06T 11/00; G06T 15/08; G06T 19/00; G06T 2207/10141; G06T 2207/20092; G06T 2207/20221; G06T 2207/30096; G06T 2207/30104; G06T 2210/41; G06T 2211/404; G06T 7/0016; G06T 7/136; G06T 7/194; G06T 7/60; H01P 1/185; H01P 5/18; A61B 6/027; A61B 3/1025; A61B 3/1241; A61B 3/14; A61B 3/102; A61B 3/0091; A61B 3/0025; A61B 2576/02; A61B 3/0041; A61B 3/12;
(Continued)

(56) References Cited

U.S. PATENT DOCUMENTS

2007/0268993 A1* 11/2007 Forthmann ........... G06T 11/005 378/4
2008/0317308 A1* 12/2008 Wu ...................... G06K 9/4638 382/128

(Continued)

FOREIGN PATENT DOCUMENTS

JP    2015531274 A    11/2015

*Primary Examiner* — Aklilu K Woldemariam
(74) *Attorney, Agent, or Firm* — Canon U.S.A., Inc. IP Division

(57) ABSTRACT

The position of the fovea is estimated with high accuracy in a manner such that the thicknesses of a first region including at least a partial region of a region from the internal limiting membrane to the boundary between the external plexiform layer and the external granular layer and a second region including at least a partial region of a region from the boundary to the photoreceptor cell inner segment/outer segment junction are compared with each other, and the position of the fovea is estimated.

29 Claims, 20 Drawing Sheets

(51) Int. Cl.
*G06T 7/11* (2017.01)
*G06T 7/00* (2017.01)
*G06T 11/00* (2006.01)

(52) U.S. Cl.
CPC .. *G06T 11/003* (2013.01); *G06T 2207/10101* (2013.01); *G06T 2207/20116* (2013.01); *G06T 2207/30041* (2013.01)

(58) Field of Classification Search
CPC . A61B 5/0033; A61B 5/0073; A61B 5/02007; A61B 5/066; G06K 9/00604; G01B 2290/70; G01B 9/02028; G01B 9/0203; G01B 9/02068; G01B 9/02087; G01B 9/02091; G02B 21/0028
USPC ......... 382/128, 129, 130, 131, 132; 351/206
See application file for complete search history.

(56) References Cited

U.S. PATENT DOCUMENTS

| | | | |
|---|---|---|---|
| 2011/0211057 A1* | 9/2011 | Iwase | A61B 3/102 348/78 |
| 2012/0070049 A1* | 3/2012 | Iwase | G06T 7/0012 382/128 |
| 2012/0148130 A1* | 6/2012 | Nakano | G06T 7/11 382/131 |
| 2012/0218517 A1* | 8/2012 | Imamura | A61B 3/1241 351/206 |
| 2014/0063458 A1* | 3/2014 | Imamura | A61B 3/14 351/206 |
| 2014/0086383 A1* | 3/2014 | Huwer | A61B 6/505 378/5 |
| 2014/0121506 A1* | 5/2014 | Iwase | G01B 9/02028 600/425 |
| 2014/0152396 A1* | 6/2014 | Fackelmeier | H01P 5/18 333/116 |
| 2014/0307933 A1* | 10/2014 | Knighton | A61B 3/102 382/131 |
| 2015/0116664 A1* | 4/2015 | Uchida | A61B 3/0025 351/206 |
| 2015/0371414 A1* | 12/2015 | Choi | G06T 11/005 382/131 |
| 2016/0256127 A1* | 9/2016 | Lee | A61B 6/032 |

* cited by examiner

FIG. 6A
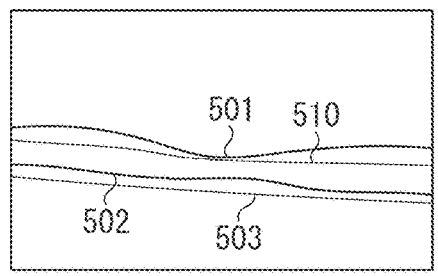
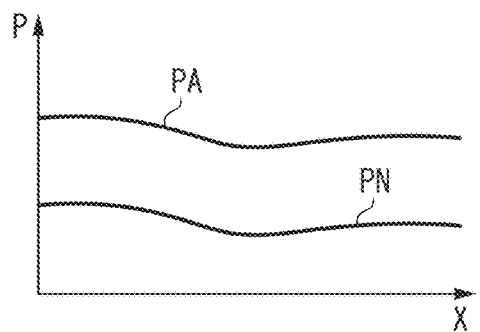
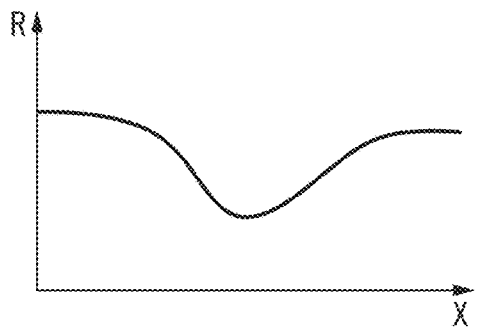
FIG. 6B
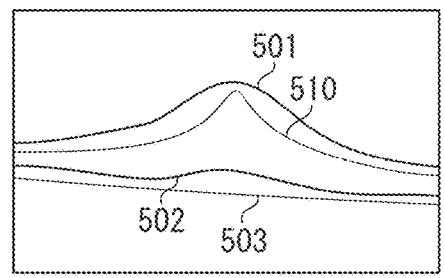
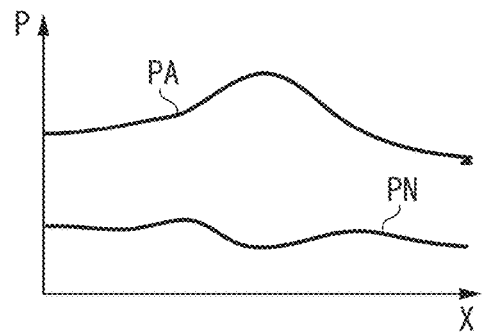
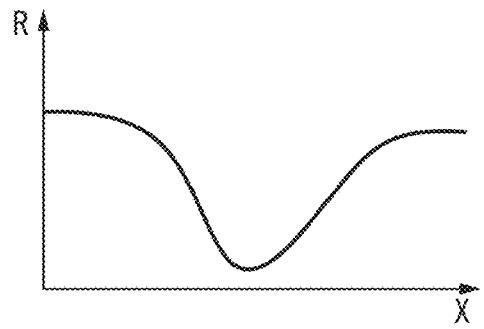

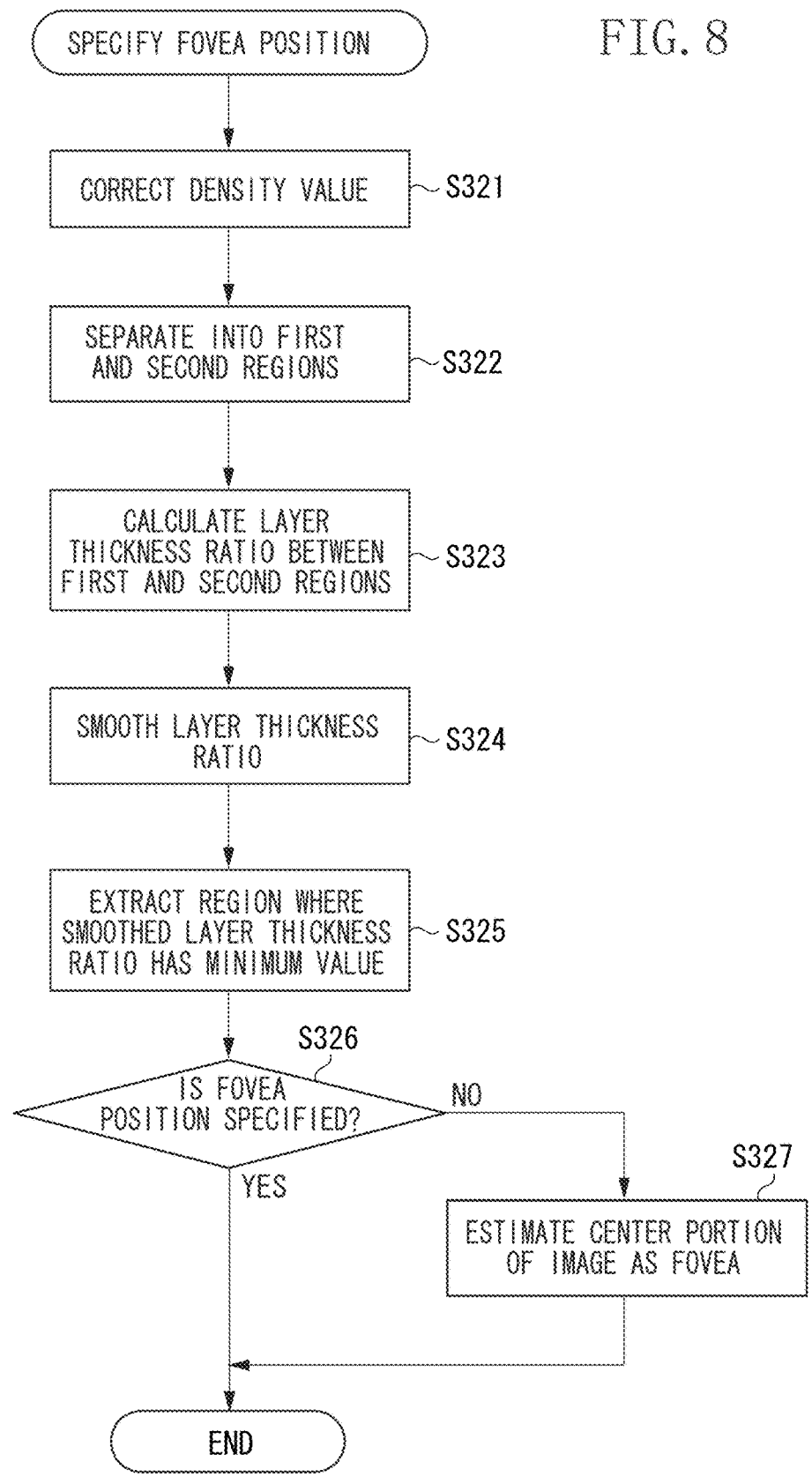

US 10,251,548 B2

IMAGE PROCESSING APPARATUS, ESTIMATION METHOD, SYSTEM, AND MEDIUM

BACKGROUND

Field

This disclosure relates to an image processing apparatus, an estimation method, a system, and a medium.

Description of the Related Art

A fovea is a region present in a center portion of a macula and having a diameter of about 0.4 mm, and is observed as a depressed region in a tomographic image of a healthy eye. Further, the closer to the fovea, the higher the density of photoreceptor cells in charge of the visual performance. Thus, there is a possibility that the closer to the fovea a lesion is, the greater the influence of the lesion on the visual performance. Thus, to accurately diagnose the state of a subject's eye, it is important to know the position of the fovea.

Japanese Unexamined Patent Application Publication No. 2015-531274 discusses, as a method for estimating the position of the fovea, a method for determining the deepest portion of an internal limiting membrane (ILM) as the fovea, and a method for determining, as the fovea, the position where a distance between the ILM and a retinal pigment epithelium (RPE) layer is shortest.

SUMMARY

A technique according to an aspect of the disclosure accurately estimates the position of the fovea even in a case where a depressed region loses its shape.

The technique according to such aspect of the disclosure may also obtain an operation and an effect that result from the configurations illustrated in the description of the embodiments below and cannot be obtained by a conventional technique.

According to an aspect of the disclosure, an image processing apparatus includes an acquisition unit configured to acquire a tomographic image of a fundus, a determination unit configured to determine a first region and a second region by analyzing the tomographic image, the first region including at least a partial region of a region from an internal limiting membrane to a boundary between an external plexiform layer and an external granular layer, the second region including at least a partial region of a region from the boundary to a photoreceptor cell inner segment/outer segment junction, a comparison unit configured to compare a thickness of the first region with a thickness of the second region in a depth direction of the tomographic image, and an estimation unit configured to estimate a position of a fovea based on a result of the comparison by the comparison unit.

Further features of the present invention will become apparent from the following description of exemplary embodiments with reference to the attached drawings.

BRIEF DESCRIPTION OF THE DRAWINGS

FIGS. 6A and 6B are diagrams each illustrating an example of a layer thickness ratio.

FIG. 8 is a flowchart illustrating an example of a procedure for estimating the fovea position.

DESCRIPTION OF THE EMBODIMENTS

As described above, the conventional method for estimating the position of the fovea is based on the premise that the fovea is located in a depressed region in a tomographic image. That is, the conventional method for estimating the position of the fovea is based on the premise that a target from which the fovea position is extracted is a tomographic image of a healthy eye.

Figure 20:
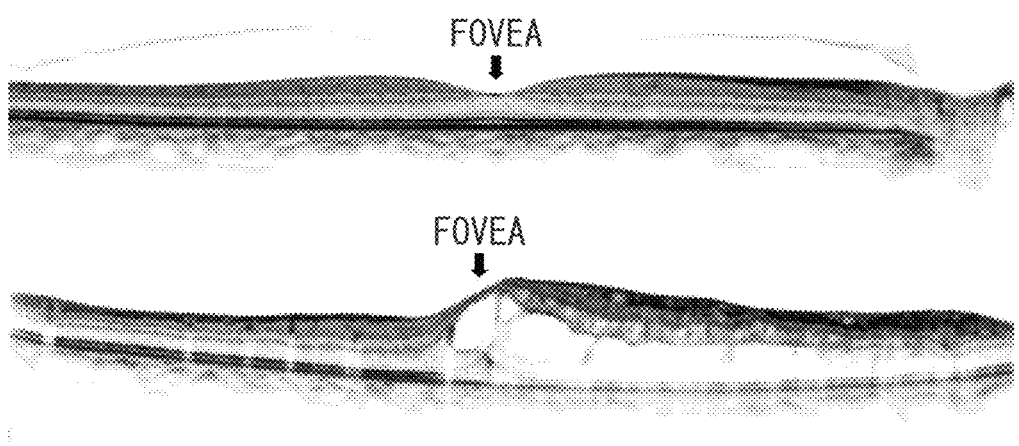
FIG. 20 is a diagram illustrating examples of a tomographic image of a healthy eye and a tomographic image of an eye affected by illness.

Thus, for example, as illustrated in FIG. 20, in a case where a depressed region loses its shape as a result of deformation of a retina due to illness, it may not be possible to accurately estimate the position of the fovea using the conventional method.

In view of the above problem, a technique according to an aspect of the disclosure accurately estimates the position of the fovea even in a case where a depressed region loses its shape.

Figure 1:
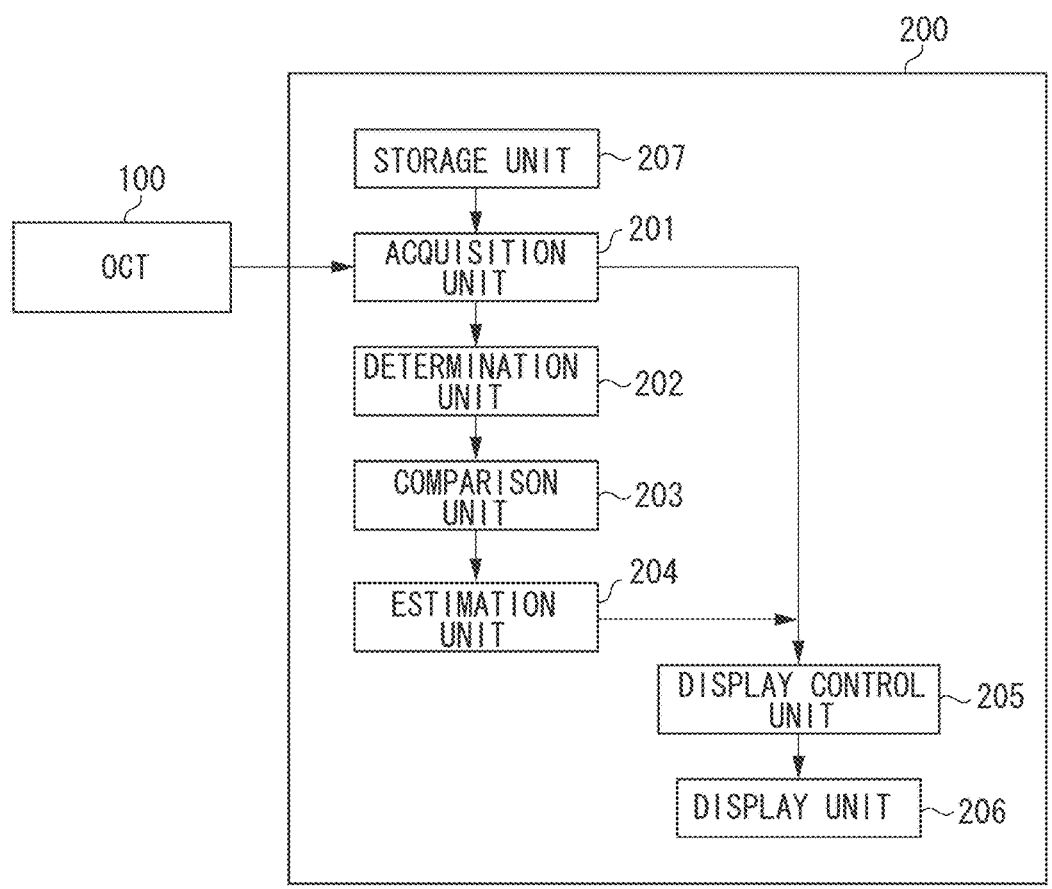
FIG. 1 is a diagram illustrating an example of a configuration of a system.

FIG. 1 is a diagram illustrating an example of a configuration of a system for estimating the position of the fovea according to a first exemplary embodiment. The system illustrated in FIG. 1 includes an optical coherence tomography spectrometer (OCT) 100 and an image processing apparatus 200. The OCT 100 and the image processing apparatus 200 are connected together via a wired or wireless connection so that the OCT 100 and the image processing apparatus 200 can communicate with each other.

The OCT 100 is an OCT apparatus capable of capturing a tomographic image of a fundus of a subject's eye. The OCT 100 may be an OCT of the type of either time-domain OCT (TD-OCT) or spectral-domain OCT (SD-OCT). Alternatively, the OCT 100 may be an OCT of a type of either swept-source OCT (SS-OCT) or polarization-sensitive OCT (PS-OCT). The OCT 100 acquires a tomographic image representing a section of a retina, using the interference between reference light and light returning from the fundus obtained by scanning the fundus with near-infrared light (measurement light). That is, the OCT 100 acquires a tomographic image of a fundus. In the specification, a scan for acquiring a one-dimensional tomographic image in a depth direction at any point on a subject's eye will occasionally be referred to as an "A-scan", and a tomographic image generated by an A-scan will occasionally be referred to as an "A-scan image". Further, in the specification, a scan for acquiring a two-dimensional tomographic image along any line will occasionally be referred to as a "B-scan", and a tomographic image acquired by a B-scan will occasionally be referred to as a "B-scan image".

The OCT 100 outputs the acquired tomographic image and imaging information (a type of the image, an imaged part, a position of a fixation lamp, an imaging size, and a scanning pattern) to the image processing apparatus 200 via a wired or wireless connection (e.g., via a Universal Serial Bus (USB) connection or a wireless local area network (LAN)). The imaging information includes, for example, information indicating "OCT" as the type of the image, "macular portion" as the imaged part, "12 mm" as the imaging size, and "line scan" as the scanning pattern. Further, the imaging information may include the coordinates of the position of the fixation lamp. The imaging information is not limited to this. Alternatively, not all the above information necessarily needs to be included in the imaging information, or another piece of information may be included in the imaging information. The information indicating the type of the image may include not only "OCT" but also the type of the OCT, such as SD-OCT, SS-OCT, or PS-OCT. Yet alternatively, the unit of the imaging size may be not a length but an angle (an angle of view). The imaging information may be information associated with the tomographic image and not regarding the tomographic image, or may be included as metadata in a header of the tomographic image or the like.

The image processing apparatus 200 estimates the position of the fovea from the tomographic image obtained by the OCT 100. The image processing apparatus 200 is, for example, a desktop personal computer (PC), a laptop PC, or a tablet PC. The image processing apparatus 200 includes a central processing unit (CPU), a read-only memory (ROM), and a random-access memory (RAM). The CPU achieves various functions by loading a program stored in the ROM into the RAM. Specifically, the CPU of the image processing apparatus 200 functions as an acquisition unit 201, a determination unit 202, a comparison unit 203, an estimation unit 204, and a display control unit 205.

The image processing apparatus 200 may include a single CPU and a single memory for each of a ROM and a RAM, or may include a plurality of CPUs and a plurality of memories for ROMs or RAMs. That is, in a case where at least one or more processors (e.g., CPU) and at least one or more memories (e.g., ROM and RAM) are connected together, and the at least one or more processors execute a program stored in the at least one or more memories, the image processing apparatus 200 functions as the above units. Alternatively, at least some of the above functions may be achieved by an application-specific integrated circuit (ASIC) or a field programmable gate array (FPGA) instead of the CPUs.

Further, the image processing apparatus 200 includes a display unit 206 and a storage unit 207. In the present exemplary embodiment, the display unit 206 and the storage unit 207 are provided in the image processing apparatus 200. Alternatively, at least one of the display unit 206 and the storage unit 207 may be provided outside the image processing apparatus 200. That is, the display unit 206 may be integrated with or separate from the image processing apparatus 200, which is a PC, for example. Further, the storage unit 207 may be an internal storage device or an external storage device.

The acquisition unit 201 acquires the tomographic image and the imaging information of the tomographic image transmitted from the OCT 100 to the image processing apparatus 200. That is, the acquisition unit 201 acquires a tomographic image of a fundus.

The acquisition unit 201 may be configured to save a tomographic image and imaging information of the tomographic image in advance in the storage unit 207, and according to a request from an operator, read the tomographic image and the imaging information of the tomographic image from the storage unit 207. In the present exemplary embodiment, the acquisition unit 201 acquires a tomographic image and imaging information of the tomographic image from the OCT 100.

From the tomographic image acquired by the acquisition unit 201, the determination unit 202 determines a first region including at least a partial region of a region from an internal limiting membrane (ILM) to a boundary between an external plexiform layer and an external granular layer, and a second region including at least a partial region of a region from this boundary to a photoreceptor cell inner segment/outer segment (IS/OS) junction. As an example, the determination unit 202 determines the first and second regions using a discrimination analysis method. As the discrimination analysis method, the Otsu's discrimination analysis method can be used. Alternatively, another discrimination analysis method may be used. The Otsu's discrimination analysis method is known and therefore is not described in detail. The determination unit 202 determines a threshold using the discrimination analysis method with respect to each of A-scan images included in tomographic images. That is, using the discrimination analysis method, the determination unit 202 determines a threshold for determining the first and second regions. Then, with respect to each A-scan image, the determination unit 202 determines as the first region a region in the tomographic image having a density value equal to or greater than the threshold determined using the discrimination analysis method, and determines as the second region a region in the tomographic image having a density value less than the threshold.

Alternatively, the determination unit 202 can also determine the first and second regions based not on the density value of a pixel included in the tomographic image, but on the luminance value of the pixel. For example, with respect to each A-scan image, the determination unit 202 may determine as the first region a region in the tomographic image having a luminance value equal to or greater than a threshold determined using the discrimination analysis method, and determine as the second region a region in the tomographic image having a luminance value less than the threshold. In the present exemplary embodiment, the higher the density value, the higher the luminance value. As described above, the determination unit 202 determines as the first region a region where the density or the luminance of a pixel included in a tomographic image is equal to or greater than a threshold, and determines as the second region a region where the density or the luminance of a pixel included in the tomographic image is less than the threshold. The method for determining a region using a threshold makes use of the fact that the luminance of the external granular layer is lower than the luminance of a region from the ILM to the boundary between the external plexiform layer and the external granular layer.

Alternatively, the determination unit 202 may use a region from the ILM to the IS/OS junction in the tomographic image as a processing target for determining the above first and second regions. In this case, the first and second regions are included in the range from the ILM to the IS/OS junction. For example, the determination unit 202 detects the IS/OS junction from the tomographic image and deletes an image of a portion deeper than the IS/OS junction, and can limit a processing target for determining the first and second regions. Yet alternatively, the determination unit 202 may use a region from the ILM to the external limiting membrane (ELM) in the tomographic image as a processing target for determining the above first and second regions.

The comparison unit 203 compares the thickness of the first region with the thickness of the second region in the depth direction of the tomographic image. More specifically, the comparison unit 203 compares the thickness of the first region with the thickness of the second region with respect to each A-scan image. As a result of the comparison, the comparison unit 203 outputs, for example, a value indicating the ratio between the thickness of the first region and the thickness of the second region. Alternatively, the comparison unit 203 may output a value indicating the ratio between the thickness of the first region or the thickness of the second region and the sum of the thicknesses of the first and second regions. In the present exemplary embodiment, the comparison unit 203 outputs a value obtained by dividing the thickness of the first region by the sum of the thicknesses of the first and second regions.

The estimation unit 204 estimates the position of the fovea based on the result of the comparison by the comparison unit 203. For example, the estimation unit 204 estimates the position of the fovea based on an extreme point of a value indicated by the result of the comparison by the comparison unit 203. As an example, the estimation unit 204 estimates as the position of the fovea a portion indicating that the thickness of the first region relative to the thickness of the second region in the tomographic image is the smallest. In the present exemplary embodiment, the estimation unit 204 estimates, as the position of the fovea, the position in the tomographic image where a value obtained by dividing the thickness of the first region by the sum of the thicknesses of the first and second regions is at a minimum. In a case where the comparison unit 203 outputs as the comparison result a value obtained by dividing the thickness of the second region by the sum of the thicknesses of the first and second regions, the estimation unit 204 estimates, as the position of the fovea, the position in the tomographic image where a value obtained by dividing the thickness of the second region by the sum of the thicknesses of the first and second regions is at a maximum.

The display control unit 205 causes the display unit 206 to display various pieces of information. For example, the display control unit 205 causes the display unit 206 to display information indicating the position of the fovea estimated by the estimation unit 204 on the tomographic image acquired by the acquisition unit 201 in a superimposed manner. The information indicating the position of the fovea includes a figure such as an arrow, a line, or a circle indicating the position of the fovea. Alternatively, the display control unit 205 may cause the display unit 206 to display information indicating the position of the fovea on a front image of the fundus in a superimposed manner.

The display unit 206 displays various pieces of information based on the control of the display control unit 205. The display unit 206 is a liquid crystal display (LCD), for example.

The storage unit 207 stores various pieces of information. The storage unit 207 includes at least one of a RAM, a ROM, a solid-state drive (SSD), and a hard disk drive (HDD), for example. The storage unit 207 stores the tomographic image and the imaging information. Further, the storage unit 207 stores the tomographic image and the information indicating the position of the fovea estimated by the estimation unit 204 in association with each other. The information indicating the position of the fovea may be included in the header of information indicating the tomographic image.

Figure 2:
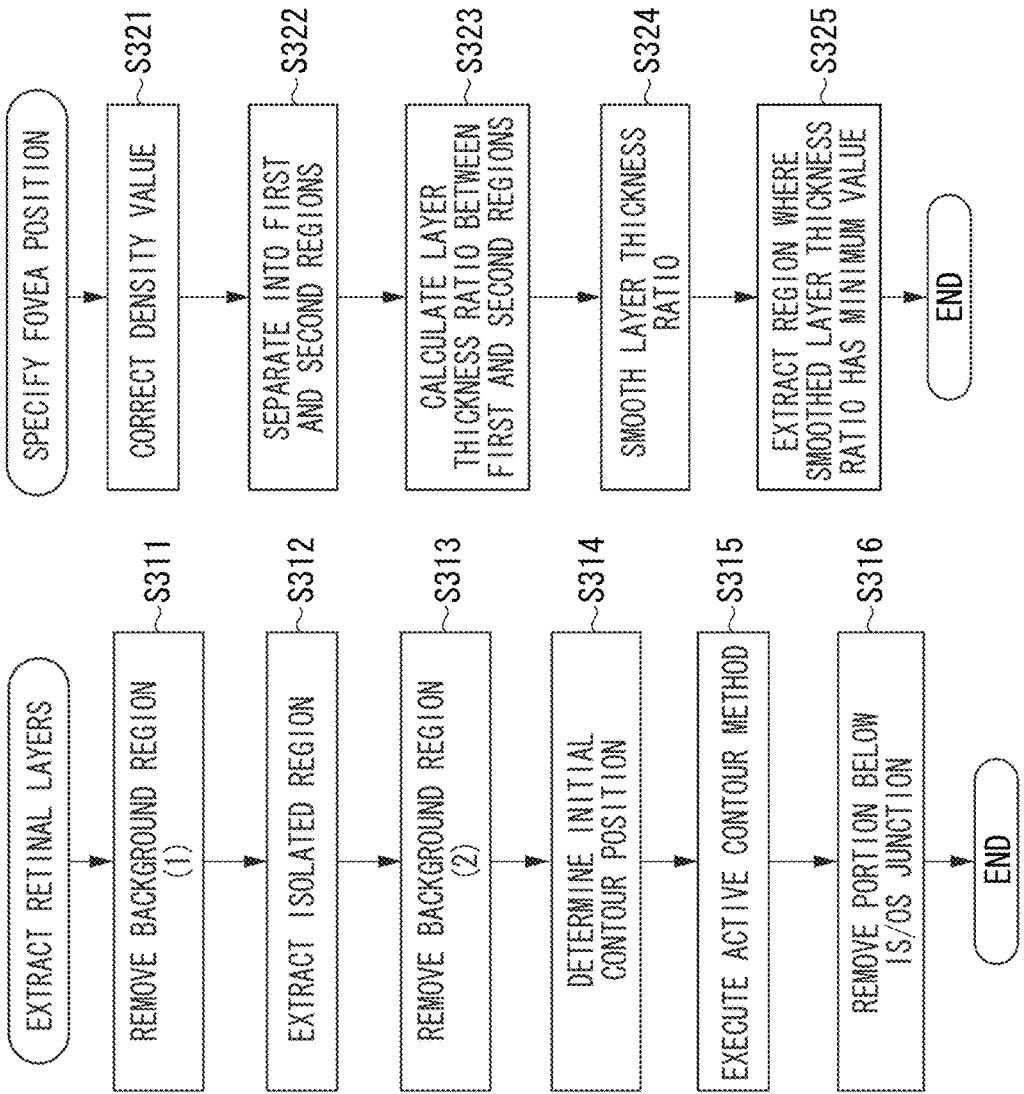
FIGS. 2A, 2B, and 2C are flowcharts illustrating an example of a procedure for estimating a fovea position.

Next, a description is given of an example of the operation of the image processing apparatus 200 having the above configuration. FIGS. 2A to 2C are flowcharts illustrating an example of the operation of the image processing apparatus 200. FIG. 2A is a flowchart illustrating a general procedure of an example of a method for estimating the position of the fovea.

In step S300, the acquisition unit 201 acquires a tomographic image (e.g., a B-scan image). Then, in step S310, the determination unit 202 extracts a retinal region (retinal layers) included in the tomographic image. Next, in step S320, the estimation unit 204 estimates the position of the fovea from the extracted retinal region. Before the process of step S310 or S320 is performed, the determination unit 202 may perform preprocessing, such as noise removal, density normalization, or correction of a center position or a tilt of the tomographic image. The preprocessing can improve accuracy of the estimation of the position of the fovea.

FIG. 2B is a flowchart illustrating an example of the detailed processing of step S310.

In step S311, the determination unit 202 scans the acquired tomographic image from its outermost portion to its center portion and removes as a background region a region up to pixels of which density values exceed a threshold. Alternatively, the determination unit 202 may not remove the background region from the image, and may set for the background region a flag indicating that the background region is not a processing target.

Figure 3:
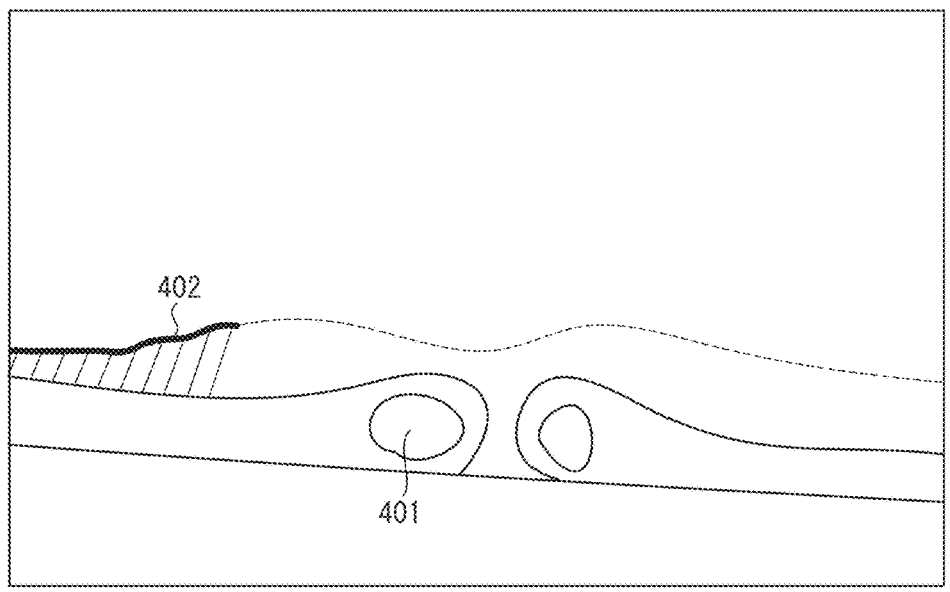
FIG. 3 is a diagram illustrating an example of a space region.

In a tomographic image illustrated in FIG. 3, a cyst 401 and the external granular layer in the retina are visualized as low-density regions. Thus, if the low-density regions are simply removed, a region in the retina is also deleted as a background region. To avoid this, the determination unit 202 scans the acquired tomographic image from its outermost portion to its center portion and determines as a background region a region up to pixels of which density values exceed a threshold.

In step S312, the determination unit 202 extracts from the tomographic image a low-density isolated region in a region left by removing the background region determined in step S311. In the present exemplary embodiment, the low-density region is a region including a pixel having a density less than a predetermined threshold in the tomographic image. If determining that the low-density isolated region is a space outside the retina, the determination unit 202 determines this space as a background region. For example, as illustrated in FIG. 3, in a case where a posterior vitreous cortex 402 having a high density is present above the retina, then in step S311, the determination unit 202 recognizes as a background region a region closer to the anterior eye segment than the posterior vitreous cortex 402 is. Thus, after the process of step S311, a space indicated as a shaded portion is left in the image. In step S312, this space is extracted as a low-density isolated region. The determination of whether the space is to be deleted (the space is outside the retina) is made based on information of at least one of the position, the shape, and the area of each isolated region. For example, normally, the position of the retina is located at approximately the center in the depth direction of a tomographic image. Thus, taking into account the thickness of the retina, the determination unit 202 sets as a reference position a position away from the center of the tomographic image to the anterior eye segment side by a predetermined value or more in the depth direction. Then, the determination unit 202 determines, as a space to be deleted, a low-density isolated region present closer to the anterior eye segment side than the reference position is. Further, a low-density isolated region in the retina is often smaller than a low-density isolated region outside the retina. Thus, if the size of a low-density isolated region is equal to or greater than a predetermined value, the determination unit 202 may determine the low-density isolated region as a space to be deleted.

In step S313, the determination unit 202 removes as a background region the region determined as the space to be deleted in step S312. In the processes of steps S311 to S313, the determination unit 202 can delete background regions from the tomographic image and extract a retinal region.

In steps S314 and S315, the determination unit 202 analyzes the retinal region extracted in step S313, extracting the ILM, the RPE, and the IS/OS junction, for example. Specifically, the determination unit 202 extracts the ILM, the RPE, and the IS/OS using an active contour method. The retina includes a plurality of layers. In a healthy eye, about 10 layers are observed. In a retina having a lesion or bleeding, however, there is a case where it is difficult to extract all the 10 layers. In response, in the present exemplary embodiment, even in a case where a lesion is present in some of the layers of the retina, the determination unit 202 extracts three layers, namely the ILM, the RPE, and the IS/OS junction, which are relatively easily detected. The layers to be extracted by the determination unit 202 are not limited to these. Alternatively, for example, the determination unit 202 may extract only the ILM and the IS/OS junction, or may extract only the ILM and the RPE.

First, in step S314, the determination unit 202 sets an initial contour position for applying the active contour method in step S315. To avoid an incorrect local solution in step S315, an appropriate initial contour position is set. Specifically, first, the determination unit 202 extracts, with respect to each X-axis coordinate, a pixel of which the density in the depth direction (a Z-axis direction) is at a minimum in the retinal region. In the present exemplary embodiment, the X-direction corresponds to the horizontal direction of a B-scan image. Next, the determination unit 202 approximates the positions of a group of the extracted pixels to a quartic approximation curve. The determination unit 202 determines this approximation curve as a retinal center line passing through a center portion of the retina. Further, the determination unit 202 performs scanning in a direction of a choroid from the retinal center line and sets a plurality of points at which the density is at a maximum, as point sequences of initial contour points of the IS/OS junction and the RPE in order from the anterior eye segment side. Further, the determination unit 202 sets, as a point sequence of initial contour points of the ILM, the upper end of the retinal region determined in step S313. In the present exemplary embodiment, a closed curve is used as the initial contour position in step S315. Thus, the determination unit 202 adds a point sequence of an end portion of the B-scan image to the determined initial contour points and determines the addition result as a final initial contour position.

In step S315, based on the initial contour position determined in step S314, the determination unit 202 determines the positions of the above three layers using the active contour method. In the present exemplary embodiment, to extract each of the retinal layers as a line that does not branch in the middle and is continuous, the active contour method is applied. In the present exemplary embodiment, as an example of an algorithm of the active contour method, snakes is used. In snakes, a shape energy Eshape and an image energy EImage are defined, and these energies are minimized by iterative calculations. The shape energy Eshape is defined such that the smoother the shape of the retinal layer, the smaller the energy. The image energy EImage is defined such that the greater the edge strength, the smaller the energy. Thus, the place where each energy is at a minimum is detected while all the points set as the initial contour position are moved, whereby it is possible to extract a layer boundary having great edge strength in a smooth shape. As described above, the determination unit 202 detects the place where each energy is at a minimum, while moving all the points set as the initial contour position, extracting the ILM, the RPE, and the IS/OS junction.

In the present exemplary embodiment, an image obtained by differentiating the tomographic image in the Z-axis direction is used as the image energy EImage. The direction in which the tomographic image is differentiated in the Z-axis direction is set to a direction in which the image energy EImage is at a minimum at the boundary between retinal layers to be extracted. Further, in the present exemplary embodiment, the contribution rate of each of continuity, image, and curvature energies is obtained experimentally and determined in advance.

Figure 4:
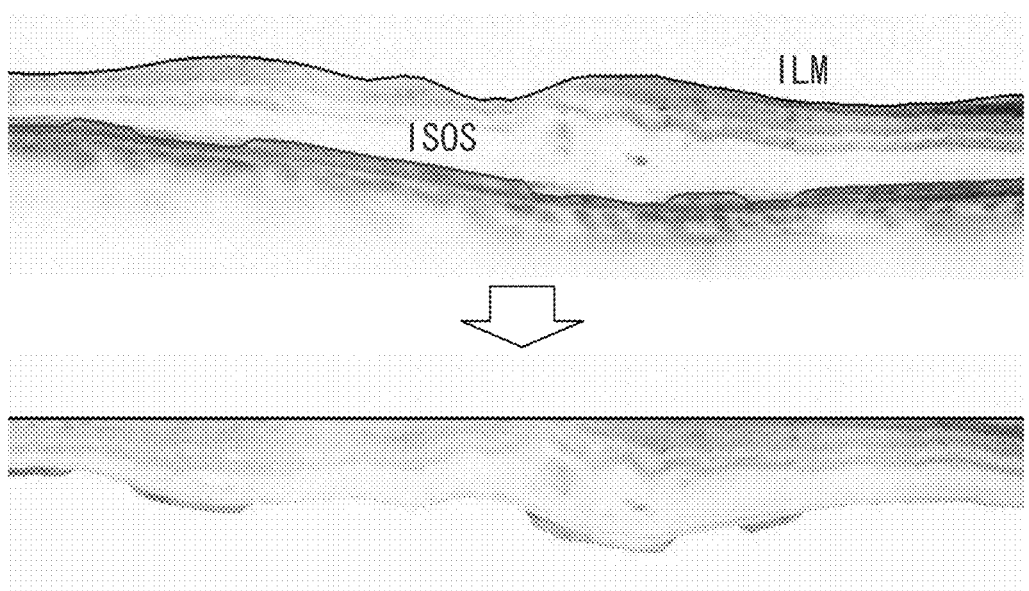
FIG. 4 is a diagram illustrating an example of processing on a tomographic image.

Next, in step S316, using the ILM and the IS/OS junction detected in step S315, the determination unit 202 acquires an image as a target of a fovea position estimation process. Specifically, as illustrated in FIG. 4, the determination unit 202 generates an image by determining the ILM as the upper end of the image (or leveling the ILM) and deleting an image of a portion which is closer to a choroid side than the IS/OS junction. The determination unit 202 may acquire an image illustrated in FIG. 4 from the image obtained by the processes of steps S311 to S313, or may acquire an image illustrated in FIG. 4 from the tomographic image acquired by the acquisition unit 201. The processing illustrated in FIG. 4 is performed to facilitate the processes of steps S321 to S325. In the processing illustrated in FIG. 4, the determination unit 202 deletes an image of a portion which is closer to the choroid side than the IS/OS junction. Alternatively, the determination unit 202 may generate an image by deleting an image of a portion which is closer to a choroid side than the RPE, instead of the IS/OS junction. Yet alternatively, in a case where the ELM is detected, the determination unit 202 may generate an image by deleting an image of a portion which is closer to the choroid side than the ELM. In addition, the process of leveling the ILM may or may not be executed.

Next, the detailed processing of a fovea position specifying process S320 is described. FIG. 2C is a flowchart illustrating an example of the detailed processing of step S320.

Generally, in the fovea, the external granular layer composed of cone cells is thick, and the external plexiform layer located above the external granular layer is thin. Further, in a tomographic image, the external plexiform layer is visualized with a higher density than the external granular layer.

Moreover, a region from the ILM to the boundary between the external plexiform layer and the external granular layer is visualized with a higher density than a region from the boundary between the external plexiform layer and the external granular layer to the IS/OS junction. Thus, based on a threshold regarding a density, the determination unit 202 can separate a first region including at least a partial region from the ILM to the boundary between the external plexiform layer and the external granular layer, and a second region including at least a partial region from this boundary to the IS/OS junction. In the present exemplary embodiment, the first and second regions are separated using the discrimination analysis method. The process of improving the accuracy of this separation is performed in step S321.

In step S321, the determination unit 202 sets the upper limit of a density value for the retinal region extracted in step S313 and replaces the density of a pixel exceeding this upper limit density value, with the upper limit density value. This is because, for example, a density value of a retinal nerve fiber layer (RNFL) in the tomographic image is very high, and therefore, if the discrimination analysis method is applied with the density value of the acquired tomographic image as it is, the RNFL and the other layers may separate from each other. As the upper limit density value, the following value may be used. For example, a region including several tens of pixels on the choroid side in the Z-axis direction from the ILM may be extracted, and the median of the density values of the extracted region may be used. Alternatively, a density value defined in advance may be uniformly used. In a case where a high-density region, such as the RNFL, can be excluded from the image, this step may not be executed.

Figure 5:
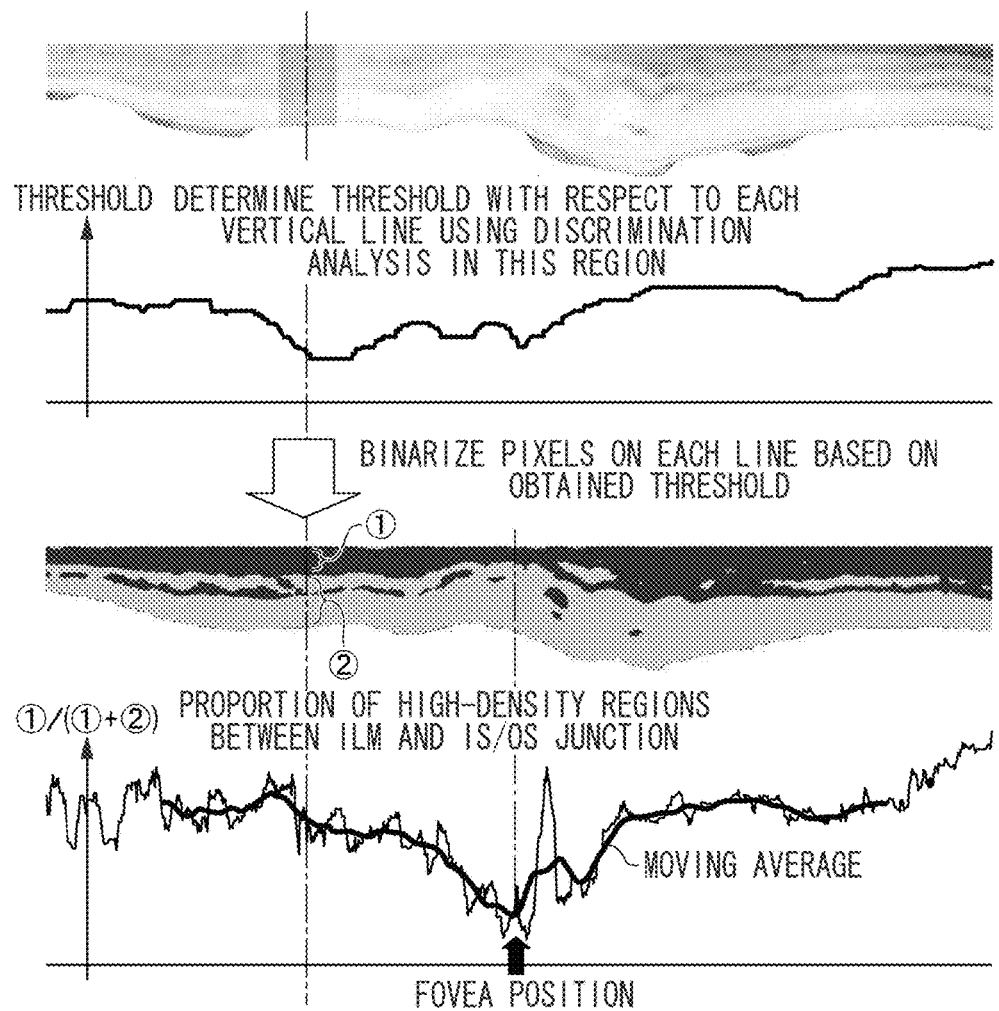
FIG. 5 is a diagram illustrating an example of a method for estimating the fovea.

Next, in step S322, using the discrimination analysis method, the determination unit 202 separates a first region including at least a partial region from the ILM to the boundary between the external plexiform layer and the external granular layer, and a second region including at least a partial region from this boundary to the IS/OS junction. Further, in a tomographic image, the luminance or the contrast fluctuates depending on the imaging condition, and further, unevenness of the density is large. Thus, to address such issues, a threshold for separating two layers is locally and dynamically calculated. In the present exemplary embodiment, as illustrated in FIG. 5, the threshold is determined by applying the discrimination analysis method to a region having a certain width (e.g., several tens of pixels) in the X-axis direction with its center at the position where a layer thickness ratio is calculated. Alternatively, the configuration may be such that after the discrimination analysis method is applied to a region including only the calculation position, the obtained threshold (the boundary line between two layers) is smoothed.

As illustrated in FIG. 5, for example, the determination unit 202 binarizes the image based on the threshold obtained using the discrimination analysis method, separating the retina into the first region, which is a high-density region, and the second region, which is a low-density region. Then, the determination unit 202 calculates the thickness of the first region and the thickness of the second region. Each of the first and second regions may be a region including continuous pixels or a region including discontinuous pixels. For example, in a case where low-density pixels are present discontinuously in the Z-axis direction as a result of the binarization, the second region may include these discontinuous pixels. That is, the total in the Z-axis direction of high-density pixels obtained as a result of the binarization may be used as the thickness of the first region, and the total in the Z-axis direction of low-density pixels obtained as a result of the binarization may be used as the thickness of the second region.

In step S323, based on the result of the separation in step S322, the comparison unit 203 calculates a layer thickness ratio, which is the proportion of the first region to an entire layer thickness, with respect to each position in the X-axis direction, using mathematical formula 1. The entire layer thickness is the sum of the thickness of the first region and the thickness of the second region.

$$R(x) = \frac{PN(x)}{PA(x)} \quad (1)$$

In mathematical formula 1, R(x) represents the layer thickness ratio at a coordinate x, PN(x) represents the thickness of the first region at the coordinate x, and PA(x) represents the entire layer thickness at the coordinate x. That is, PA(x) is the sum of the thickness of the first region and the thickness of the second region. In the present exemplary embodiment, in the layer thickness ratio R(x), the proportion of the thickness of the first region to the entire layer thickness is defined as the layer thickness ratio. The present exemplary embodiment, however, is not limited to this. Alternatively, for example, the proportion of the thickness of the second region to the entire layer thickness may be used as the layer thickness ratio R(x). Yet alternatively, a value obtained by dividing the thickness of the first region by the thickness of the second region may be used as the layer thickness ratio R(x). Yet alternatively, a value obtained by dividing the thickness of the second region by the thickness of the first region may be used as the layer thickness ratio R(x). That is, in the depth direction of the tomographic image of the fundus, the estimation unit 204 compares the size of the first region where the density or the luminance of a pixel included in the tomographic image is equal to or greater than a threshold, with the size of the second region where the density or the luminance of a pixel included in the tomographic image is less than the threshold.

In step S324, for the layer thickness ratio R(x) calculated in step S323, the comparison unit 203 calculates a moving average in the X-axis direction, which is a direction orthogonal to the Z-axis direction, smoothing the layer thickness ratio R(x). That is, the comparison unit 203 corresponds to an example of a calculation unit configured to calculate a moving average of results of comparing a plurality of positions in a direction orthogonal to a depth direction. The smoothing is performed for the following reason. In the retina having folds, there is a case where the thickness of each layer locally and greatly fluctuates, and a part where the layer thickness ratio is locally low is present. Thus, the smoothing is performed to prevent a portion where the layer thickness ratio is locally low from being erroneously estimated as the position of the fovea.

In the present exemplary embodiment, after the layer thickness ratio is calculated, the layer thickness ratio is smoothed based on a moving average. Alternatively, the configuration may be such that after the image is smoothed in advance, the layer thickness ratio is calculated. Yet alternatively, the layer thickness ratio may be smoothed using a method other than that of a moving average.

In step S325, as illustrated in FIG. 5, the estimation unit 204 extracts a position in the tomographic image where the smoothed layer thickness ratio has a minimum value (the position of a downward peak). Then, the estimation unit 204 estimates the extracted position as the position of the fovea. That is, the estimation unit 204 estimates the position of the fovea based on the calculated moving average.

As a result of scanning the smoothed layer thickness ratio in the X-axis direction, a single peak is obtained. The higher the peak, the more accurately the fovea position can be specified. The estimation unit 204 may calculate, for example, an indicator indicating the accuracy of the estimation of the fovea based on the height of the peak. That is, the estimation unit 204 calculates an indicator indicating the accuracy of the estimation of the fovea based on the layer thickness ratio. For example, the estimation unit 204 determines that the smaller the layer thickness ratio, the higher the accuracy of the estimation of the fovea. The indicator indicating the accuracy of the estimation of the fovea is displayed on the display unit 206 by the control of the display control unit 205. Alternatively, the estimation unit 204 may determine the degree of abnormality of the fovea based on at least one of the thickness of the first region and the thickness of the second region. The estimation unit 204 may determine, for example, that the greater the thickness of the first region at the estimated position of the fovea, the higher the degree of abnormality of the fovea. Yet alternatively, the estimation unit 204 may determine that the smaller the thickness of the second region, the higher the degree of abnormality of the fovea. Yet alternatively, the estimation unit 204 may determine, for example, that the smaller the difference between the thickness of the first region and the thickness of the second region at the estimated position of the fovea, the higher the degree of abnormality.

FIGS. 6A and 6B are diagrams each illustrating an example of a fovea estimation process. FIG. 6A is a diagram illustrating a case where the fovea position is specified from a tomographic image of a healthy eye. FIG. 6B is a diagram illustrating a case where the fovea position is estimated from a tomographic image of an eye in which epiretinal membrane occurs.

In step S310, the determination unit 202 extracts an ILM 501, an IS/OS junction 502, and a RPE 503 from the tomographic image. In step S322, the determination unit 202 extracts, for example, a boundary line 510 between a first region and a second region. Further, in step S323, the comparison unit 203 calculates the layer thickness ratio R(x) at each X-coordinate. As an example, the comparison unit 203 calculates a distance PN(x) between the ILM 501 and the boundary line 510, and a distance PA(x) between the ILM 501 and the IS/OS junction 502 and calculates the layer thickness ratio R(x) according to mathematical formula 1. As illustrated in FIG. 6B, for example, also in an eye in which epiretinal membrane occurs, the layer thickness ratio R(x) still has a tendency to be low near the fovea. Thus, the estimation unit 204 can estimate the fovea position with high accuracy not only in a healthy eye but also in an affected eye. In the present exemplary embodiment, analysis is performed using a density in a tomographic image. Alternatively, a similar effect can also be obtained using a luminance. Further, a tomographic image in which the density of the external granular layer is lower than the density of a region from the external plexiform layer to the ILM is used as a processing target. Alternatively, an image in which the density values are reversed can also be used as a processing target.

Figure 7A:
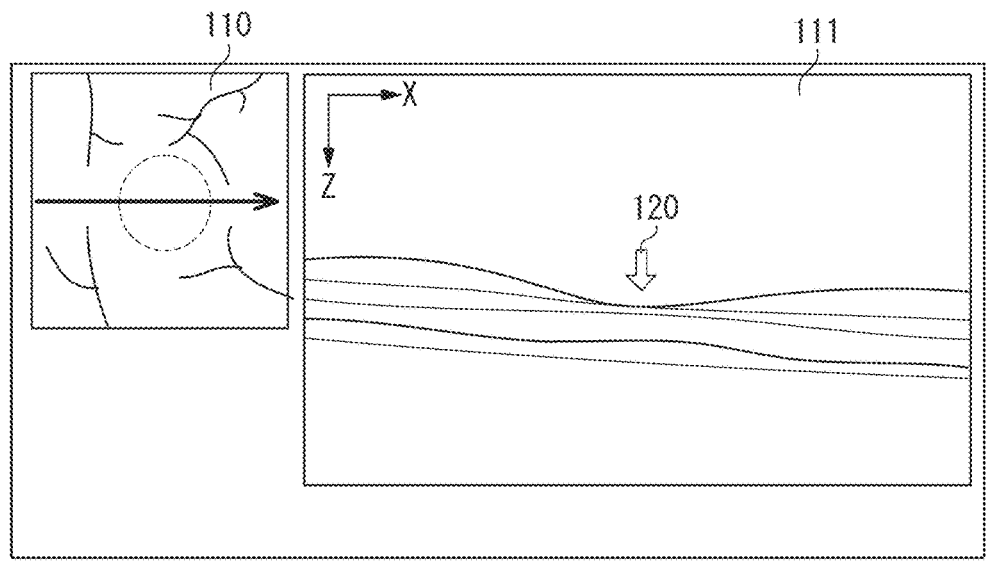
FIGS. 7A and 7B are diagrams each illustrating an example of a display screen.
Figure 7B:
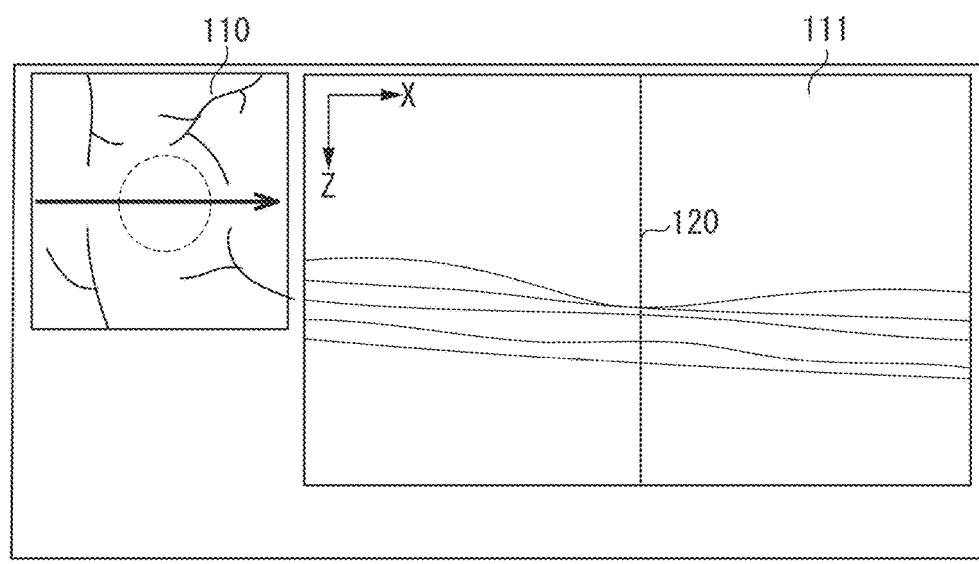

The display control unit 205 causes the display unit 206 to display the position of the fovea estimated as described above. FIGS. 7A and 7B are diagrams each illustrating an example of a screen of the display unit 206. In FIG. 7A, the display control unit 205 causes the display unit 206 to display a front image 110 and a tomographic image 111, and also causes the display unit 206 to display a marker 120, which indicates the position of the fovea estimated by the estimation unit 204, on the tomographic image 111 in a superimposed manner. The shape of the marker 120 indicating the position of the fovea may be an arrow, or may be a line as illustrated in FIG. 7B. Alternatively, the configuration may be such that an ellipse or a circle surrounding the fovea is displayed, or coordinates on an image are displayed as numerical values.

Further, as illustrated in FIGS. 7A and 7B, the display control unit 205 may cause the display unit 206 to display on the front image 110 a marker indicating the acquisition position of the tomographic image 111. The marker indicating the acquisition position of the tomographic image 111 can be moved by an operation of the operator, and the display control unit 205 causes the display unit 206 to display the tomographic image 111 corresponding to the position of the marker indicating the acquisition position of the tomographic image 111. Further, the display control unit 205 causes the display unit 206 to display the marker 120 indicating the position of the fovea corresponding to the position of the marker indicating the acquisition position of the tomographic image 111. That is, according to the update of the position of the marker indicating the acquisition position of the tomographic image 111, the display control unit 205 updates the tomographic image 111 and the marker 120 indicating the position of the fovea.

According to the present exemplary embodiment, it is possible to accurately estimate the position of the fovea from a tomographic image of not only a healthy eye but also an affected eye.

Further, the estimated position of the fovea can be indicated on a tomographic image. Thus, a doctor can easily understand the position of the fovea even in a tomographic image of an affected eye. That is, according to the present exemplary embodiment, it is possible to assist a doctor in making a quick diagnosis.

Further, according to the present exemplary embodiment, a first region and a second region are separated from each other using a discrimination analysis method without segmenting all the layers (without recognizing all the layers). Thus, even in a case where a shape of the retina is deformed due to illness, and it is difficult to perform detailed segmentation, it is possible to accurately estimate the position of the fovea.

In the first exemplary embodiment, in step S322, the determination unit 202 separates the image into the first and second regions using the discrimination analysis method. In a first variation example, however, in a case where the determination unit 202 can detect the boundary between the external plexiform layer and the external granular layer, the determination unit 202 may divide the image into the first and second regions using the detected boundary between the external plexiform layer and the external granular layer. That is, the determination unit 202 determines the first and second regions based on a layer boundary detected from the tomographic image.

As a method for detecting a layer boundary, a known method can be used. For example, the determination unit 202 can detect a change in density or luminance in the tomographic image in the Z-axis direction and recognize as a layer boundary a portion of which the luminance greatly changes. Normally, there is a luminance difference between the external plexiform layer and the external granular layer. Thus, the determination unit 202 detects a change in density or luminance in a tomographic image in the Z-axis direction to detect the boundary between the external plexiform layer and the external granular layer. The determination unit 202 can determine as the first region a retinal region located closer to the anterior eye segment side than the boundary between the external plexiform layer and the external granular layer, and determine as the second region a region located closer to the choroid side than the boundary between the external plexiform layer and the external granular layer. The boundary between the external plexiform layer and the external granular layer may be detected in step S310, or may be detected in advance before step S310.

According to the present variation example, it is possible to estimate the position of the fovea without using a discrimination analysis method. Further, in a case where the boundary between the external plexiform layer and the external granular layer is used to create a layer thickness map, it is possible to use the result of extracting the boundary between the external plexiform layer and the external granular layer to both estimate the fovea position and create the layer thickness map.

In the first exemplary embodiment, in step S323, the comparison unit 203 calculates the ratio between the layer thickness of the first region and the sum of the layer thickness of the first region and the layer thickness of the second region. Alternatively, the comparison unit 203 may calculate the difference between the layer thickness of the first region and the layer thickness of the second region. That is, the comparison unit 203 outputs the difference between the thickness of the first region and the thickness of the second region as the result of comparison between the thickness of the first region and the thickness of the second region.

For example, in a second variation example, as illustrated in mathematical formula 2, the comparison unit 203 calculates a difference between the layer thickness of the first region and the layer thickness of the second region and specifies a region where the layer thickness of the first region is relatively thin. Thus, it is possible to achieve an effect similar to that of the first exemplary embodiment.

$$S(x)=PC(x)-PN(x) \qquad (2)$$

In mathematical formula 2, $S(x)$ represents the layer thickness difference at a coordinate x, $PN(x)$ represents the thickness of the first region at the coordinate x, and $PC(x)$ represents the thickness of the second region at the coordinate x.

The estimation unit 204 estimates, as the position of the fovea, a position where a layer thickness difference $S(x)$ is at a maximum. Alternatively, the comparison unit 203 may subtract $PC(x)$ from $PN(x)$. In this case, the estimation unit 204 estimates, as the position of the fovea, a position where the layer thickness difference $S(x)$ is at a minimum. That is, according to the present variation example, it is possible to achieve an effect almost similar to that of the first exemplary embodiment.

In the first exemplary embodiment, a target region (a region in the X-direction) of the analysis process in the tomographic image is not limited. Alternatively, a target region of the analysis process may be limited based on imaging information. Specifically, the position of the fixation lamp when an image is captured may be acquired as imaging information, and only a portion around a region in the tomographic image corresponding to the position of the fixation lamp may be used as a target of the analysis process. The process of limiting an analysis region makes use of the fact that the position of the fovea (macula) moves according to the presentation position of the fixation lamp.

For example, in a third variation example, in a case where the presentation position of the fixation lamp corresponds to the center of the capturing range (the scanning range) of the tomographic image, normally, the fovea is located near the center of the image. Thus, the above fovea position estimation process may not be performed on regions near the left and right ends of the tomographic image. For example, in a case where the presentation position of the fixation lamp corresponds to the center of an imaging region of a tomographic image, the comparison unit 203 may not compare the layer thicknesses of the first and second regions in regions near the left and right ends of the tomographic image. Alternatively, the estimation unit 204 may not use the result of the comparison by the comparison unit 203 in regions near the left and right ends of the tomographic image to estimate the position of the fovea. Yet alternatively, in a case where the presentation position of the fixation lamp corresponds to an end portion of an imaging region of a tomographic image, the above fovea position estimation process may not be performed on a region near the center of the tomographic image. That is, the estimation unit 204 estimates the fovea position based on information regarding the presentation position of the fixation lamp and the result of the comparison by the comparison unit 203.

According to the present variation example, it is possible to shorten the processing time required to estimate the position of the fovea.

In the third variation example, a target region of the analysis process is limited based on the imaging information. Alternatively, the configuration may be such that if it is possible to determine from imaging information that a fovea region is clearly not included in a tomographic image, the fovea position estimation process itself is not executed. That is, based on information regarding the presentation position of the fixation lamp, the estimation unit 204 determines whether the position of the fovea is to be estimated.

Specifically, in a fourth variation example, if the acquisition unit 201 acquires a tomographic image and imaging information including the presentation position of the fixation lamp and an imaging range, the estimation unit 204 acquires the presentation position of the fixation lamp and the imaging range used to capture the image, and roughly estimates the position of the fovea in the tomographic image. In other words, the estimation unit 204 determines whether the fovea position is included in the tomographic image as a target of the analysis process. That is, the estimation unit 204 determines whether the presentation position of the fixation lamp is included in the imaging range. If it is possible to determine that a fovea region is not included, the estimation unit 204 does not execute the fovea position estimation process itself. For example, in a case where a tomographic image is captured so as to include, between an optic disc and a macula, only the optic disc, the estimation unit 204 does not execute the fovea position estimation process.

In a case where an image capture mode for capturing a tomographic image to include, between the optic disc and the macula, only the optic disc is provided in advance in the OCT 100, and information indicating a tomographic image captured in this image capture mode is included in imaging information, the estimation unit 204 determines, without using information of the presentation position of the fixation lamp and based on information of the image capture mode, that the fovea position estimation process is not to be executed.

According to the present variation example, it is possible to prevent an unnecessary fovea estimation process from being executed. Further, the display control unit 205 may cause the display unit 206 to display notification that a fovea region is not included in a tomographic image as a target of the analysis process. Consequently, for example, in a case where it is necessary to make a determination regarding a large number of tomographic images at a time as in screening, it is possible to shorten the time required for the determination.

In a second exemplary embodiment, a description is given of processing in a case where the estimation of the fovea position is failed in step S325 in the configuration of the first exemplary embodiment. FIG. 8 is a flowchart illustrating an example of a fovea position estimation process according to the present exemplary embodiment. The processes of steps S321 to S325 are similar to those in the first exemplary embodiment and therefore are not described in detail here. In step S325, when the smoothed layer thickness ratio is scanned in the X-axis direction, and in a case where a plurality of peaks having similar heights are present, or in a case where only a single peak is present but the peak has a small height and is unclear, it may not be possible to estimate the position of the fovea with high accuracy. Thus, in step S326, based on the number of peaks and the heights of the peaks, the estimation unit 204 determines whether the estimation of the fovea position is successful. For example, if, as a result of scanning the smoothed layer thickness ratio in the X-axis direction, a single peak is present, and the height of the peak is sufficient to specify the fovea position, the estimation unit 204 determines that the position of the fovea is successfully estimated. If it is determined that the fovea position is successfully specified (YES in step S326), the fovea position specifying process S320 ends.

If, on the other hand, as a result of scanning the smoothed layer thickness ratio in the X-axis direction, a plurality of peaks having similar heights are present, or only a single peak is present but the peak has a small height and is unclear, the estimation unit 204 determines that the fovea position cannot be estimated. If it is determined that the fovea position cannot be estimated (NO in step S326), then in step S327, the estimation unit 204 estimates the center of the tomographic image as the position of the fovea. That is, in a case where the position of the fovea cannot be estimated based on the result of comparison of the layer thicknesses, the estimation unit 204 estimates the center of the tomographic image as the position of the fovea.

This is because in general OCT imaging, there are many occasions where a macular portion is mainly captured, and therefore, generally, the fovea is considered to be present around a center portion of an image. In this case, the estimation unit 204 estimates a center portion of the image as the fovea, and then, the fovea position specifying process S320 ends.

Similarly to the first exemplary embodiment, the display control unit 205 causes the display unit 206 to display the marker 120 indicating the fovea position on the tomographic image in a superimposed manner. The accuracy of the estimation, however, may differ between the case where the estimation of the fovea position is successful in step S325 and the case where the fovea position is estimated in step S327. Thus, the display control unit 205 may vary the display form of the marker 120 indicating the fovea position. Also in the following exemplary embodiments, depending on a method for estimating the fovea position, the display form of the marker 120 indicating the fovea position may be changed. Further, in a case where the fovea position is estimated in step S327, the display control unit 205 may cause the display unit 206 to display a message that the center of the image is estimated as the fovea position.

According to the present variation example, even in a case where the estimation of the fovea position based on the layer thickness ratio is failed, it is possible to estimate the fovea position and therefore improve robustness.

In the second exemplary embodiment, in a case where the specifying of the fovea position based on the layer thickness ratio is failed, the center of an analysis target image is unconditionally estimated as the fovea position. Alternatively, instead of this process, the process of estimating the fovea position using imaging information may be performed. More specifically, for example, based on the presentation position of the fixation lamp and an imaging range included in imaging information, the estimation unit 204 determines a region in a tomographic image corresponding to the presentation position of the fixation lamp and estimates the determined region as the position of the fovea. That is, in a fifth variation example, in a case where the position of the fovea cannot be estimated based on the result of comparison of the layer thicknesses, the estimation unit 204 estimates the position of the fovea based on information regarding the presentation position of the fixation lamp.

According to the present variation example, even in a case where the estimation of the fovea position based on the layer thickness ratio is failed, it is possible to estimate the fovea position and therefore improve robustness. Further, according to the present variation example, even in a case where the fovea is not located at the center of a tomographic image, it is possible to estimate the fovea position with high accuracy.

In the second exemplary embodiment, in a case where the specifying of the fovea position based on the layer thickness ratio is failed, the center of an analysis target image is unconditionally estimated as the fovea position. Alternatively, instead of this process, the process of estimating as the fovea position a portion where the layer thickness is at a minimum (i.e., a depressed portion) may be executed. For example, in a sixth variation example, the estimation unit 204 may estimate as the position of the fovea a position where a distance between the ILM and the IS/OS junction extracted in step S315 is at a minimum. Alternatively, the estimation unit 204 may estimate as the position of the fovea a position where the distance between the ILM and the RPE is at a minimum.

According to the present variation example, even in a case where the estimation of the fovea position based on the layer thickness ratio is failed, it is possible to estimate the fovea position and therefore improve robustness. Further, according to the present variation example, even in a case where the fovea is not located at the center of a tomographic image, it is possible to estimate the fovea position with high accuracy.

The estimation unit 204 may successively execute the present variation example and the second exemplary embodiment, or may successively execute the present variation example and the fifth exemplary embodiment.

In the first and second exemplary embodiments, the configuration is such that the fovea position estimation process based on the layer thickness ratio is executed first on the tomographic image acquired by the acquisition unit 201. Alternatively, before the fovea position estimation process based on the layer thickness ratio, another fovea position estimation process may be executed. In a third exemplary embodiment, as an example of another fovea position estimation process, an estimation process is employed that makes use of the fact that the fovea in a healthy eye is observed as a depressed region.

Figure 9:
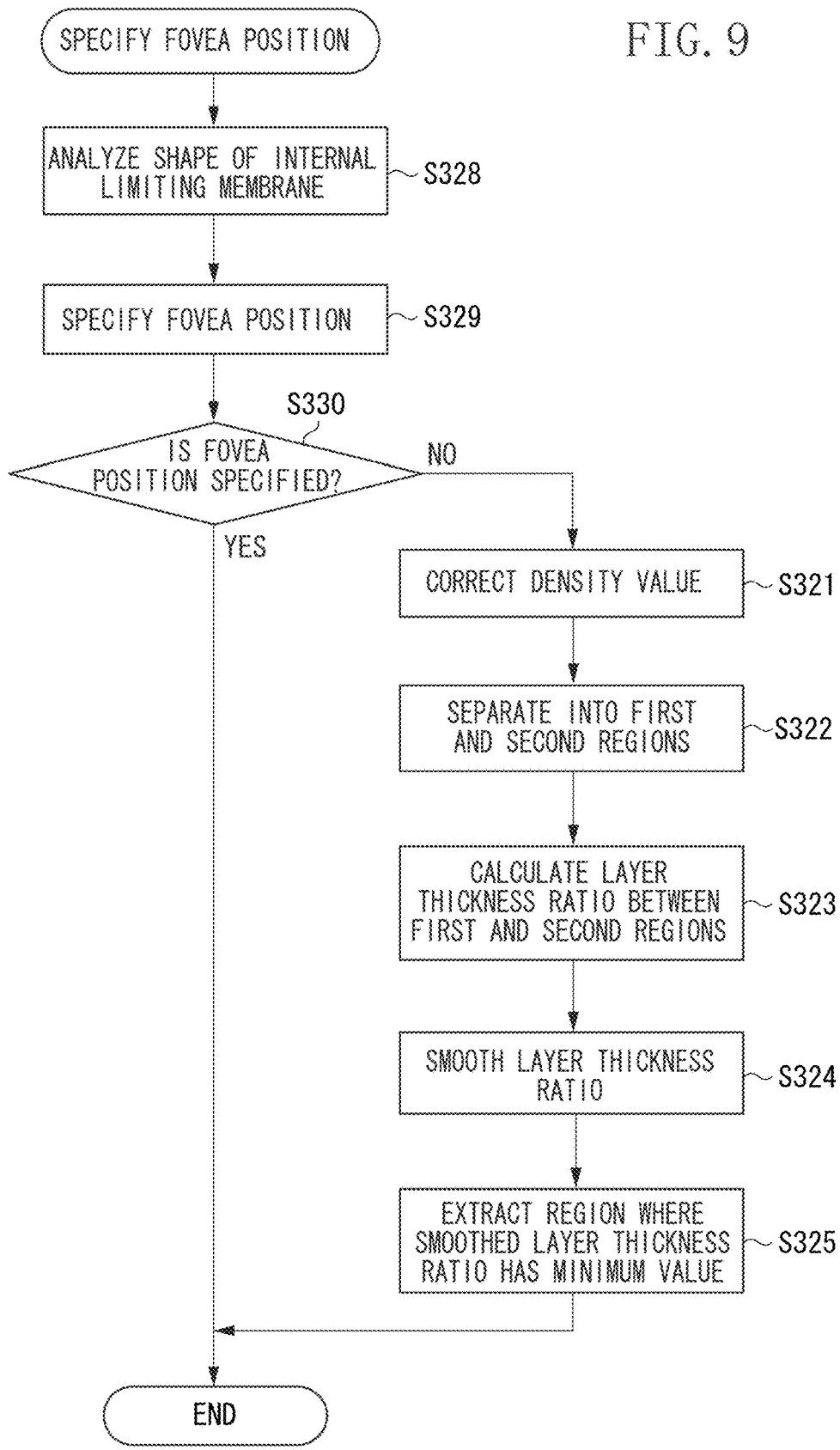
FIG. 9 is a flowchart illustrating an example of a procedure for estimating the fovea position.

FIG. 9 is a flowchart illustrating an example of the procedure of a fovea position estimation process according to the present exemplary embodiment. The processes of steps S321 to S325 are similar to those in the first exemplary embodiment and therefore are not described in detail here.

In step S328, based on layer boundary information of the ILM extracted by the determination unit 202 in step S315, the estimation unit 204 searches for a depressed portion in the tomographic image. That is, the determination unit 202 corresponds to an example of a detection unit configured to detect a layer boundary included in a tomographic image.

Next, in step S329, for example, the estimation unit 204 calculates a point at which a Z-axis coordinate of a line extracted as the ILM is at a local minimum and a minimum. Then, the estimation unit 204 estimates the calculated point as the fovea position. In the present exemplary embodiment, the closer to the choroid, the smaller the value of the Z-axis coordinate.

Further, in step S330, the estimation unit 204 obtains a difference between the Z-coordinate of the ILM at the position where the Z-coordinate is at a local minimum and a minimum, and a Z-coordinate of the ILM at another position, to determine whether the depressed portion is sufficient to specify as the fovea. For example, the estimation unit 204 compares the Z-coordinate of the ILM at the position where the Z-coordinate is at a local minimum and a minimum, with a Z-coordinate of the ILM at a position several tens to several hundreds of pixels away from the above position in the X-axis direction to determine whether the depressed portion is sufficient to specify as the fovea. The number of pixels from the position where the Z-coordinate is at a local minimum to the position used for the determination may be determined taking into account resolution of the tomographic image or an imaging condition, or may be a uniform number of pixels. For example, if a difference in the Z-coordinates is equal to or greater than a predetermined threshold in step S330, the estimation unit 204 determines that the fovea position is successfully estimated (YES in step S330). If, on the other hand, the difference in the Z-coordinates is less than the predetermined threshold in step S330, the estimation unit 204 determines that a fovea position cannot be estimated (NO in step S330), and the processing proceeds to step S321. Then, the estimation unit 204 performs the method according to the first exemplary embodiment. That is, the estimation unit 204 estimates the fovea position based on the detected layer boundary (ILM). In a case where the fovea position cannot be estimated based on the layer boundary, the estimation unit 204 estimates the fovea position based on the result of the comparison unit 203 comparing the layer thicknesses.

According to the present exemplary embodiment, it is possible to improve the robustness of the fovea position estimation process. In the present exemplary embodiment, the point at which the Z-axis coordinate of the ILM is at a local minimum and a minimum is used to estimate the fovea position. Alternatively, for example, a point at which the thickness of a RNFL is at a minimum may be used to estimate the fovea position. Yet alternatively, a point at which a distance between the RNFL and another layer, such as the ILM or the IS/OS junction, is at a minimum may be used to estimate the position of the fovea. Further, in the present exemplary embodiment, the fovea position is determined based only on layer boundary information. Alternatively, as illustrated in the first and second exemplary embodiments, the configuration may be such that the fovea position is determined also taking into account imaging information, such as the position of the fixation lamp. For example, in a case where the position in the tomographic image where a Z-coordinate of the ILM is at a local minimum and a minimum is equal to the fovea position in the tomographic image included in imaging information and estimated from information of the presentation position of the fixation lamp and an imaging range, or in a case where the difference between these positions is within a predetermined threshold, the estimation unit 204 may estimate as the position of the fovea the position in the tomographic image where the Z-coordinate of the ILM is at a local minimum and a minimum. Consequently, it is possible to estimate the fovea position from both imaging information and information of the shape of a layer and therefore improve the accuracy of the estimation of the fovea position.

In the third exemplary embodiment, before the fovea position estimation process based on the layer thickness ratio, the fovea position is estimated using layer boundary information. Alternatively, another method may be used. It is known that if observed from the front of an eyeball as in a fundus image captured by a fundus camera, a fovea in a healthy eye is observed as a dark portion. Thus, for example, in a seventh variation example, the estimation unit 204 may generate an image by integrating pixel values (luminance values or density values) of the tomographic image in the Z-axis direction, and estimate the darkest position as the fovea. In the present variation example, the estimation unit 204 compares the luminance value of the estimated position of the fovea with the luminance value of another position in the integrated image and can determine whether there is a luminance difference sufficient to estimate the fovea position. That is, the estimation unit 204 determines whether the absolute value of a difference between the luminance value of the estimated position of the fovea and the luminance value of another position is equal to or greater than a threshold. Then, if the difference is less than the threshold, the estimation unit 204 determines that the extracted position is not the fovea. Then, the estimation unit 204 performs the method for estimating the fovea position according to the first exemplary embodiment. That is, the estimation unit 204 estimates the fovea position based on the integrated value of luminance or density of a tomographic image in the depth direction. Then, in a case where the fovea position cannot be estimated based on the integrated value, the estimation unit 204 estimates the fovea position based on the result of the comparison by the comparison unit 203.

According to the present variation, it is possible to achieve an effect similar to that of the third exemplary embodiment.

In the above description, the configuration is such that if the specifying of the fovea position based on the layer boundary information or the integrated image is failed, the method according to the first exemplary embodiment is simply performed. Alternatively, another configuration may be employed. For example, in an eighth variation example, based on the integrated image, the estimation unit 204 extracts one or more candidates for the fovea position. That is, the estimation unit 204 determines as a candidate for the fovea position a portion of which the luminance is the lowest in the integrated image. Then, next, the estimation unit 204 limits in the tomographic image the processing range around the extracted candidate for the fovea position and performs the fovea estimation method according to the first exemplary embodiment. Consequently, it is possible to speed up the process of estimating the fovea position and also specify the fovea position based on a plurality of pieces of information, such as the luminance of an integrated image and the layer thickness ratio of a tomographic image. Thus, it is possible to improve the accuracy of specifying the fovea position. Instead of the position where the luminance value of the integrated image is at a minimum, a position where a Z-coordinate of the ILM is at a local minimum and a minimum may be used.

Figure 10:
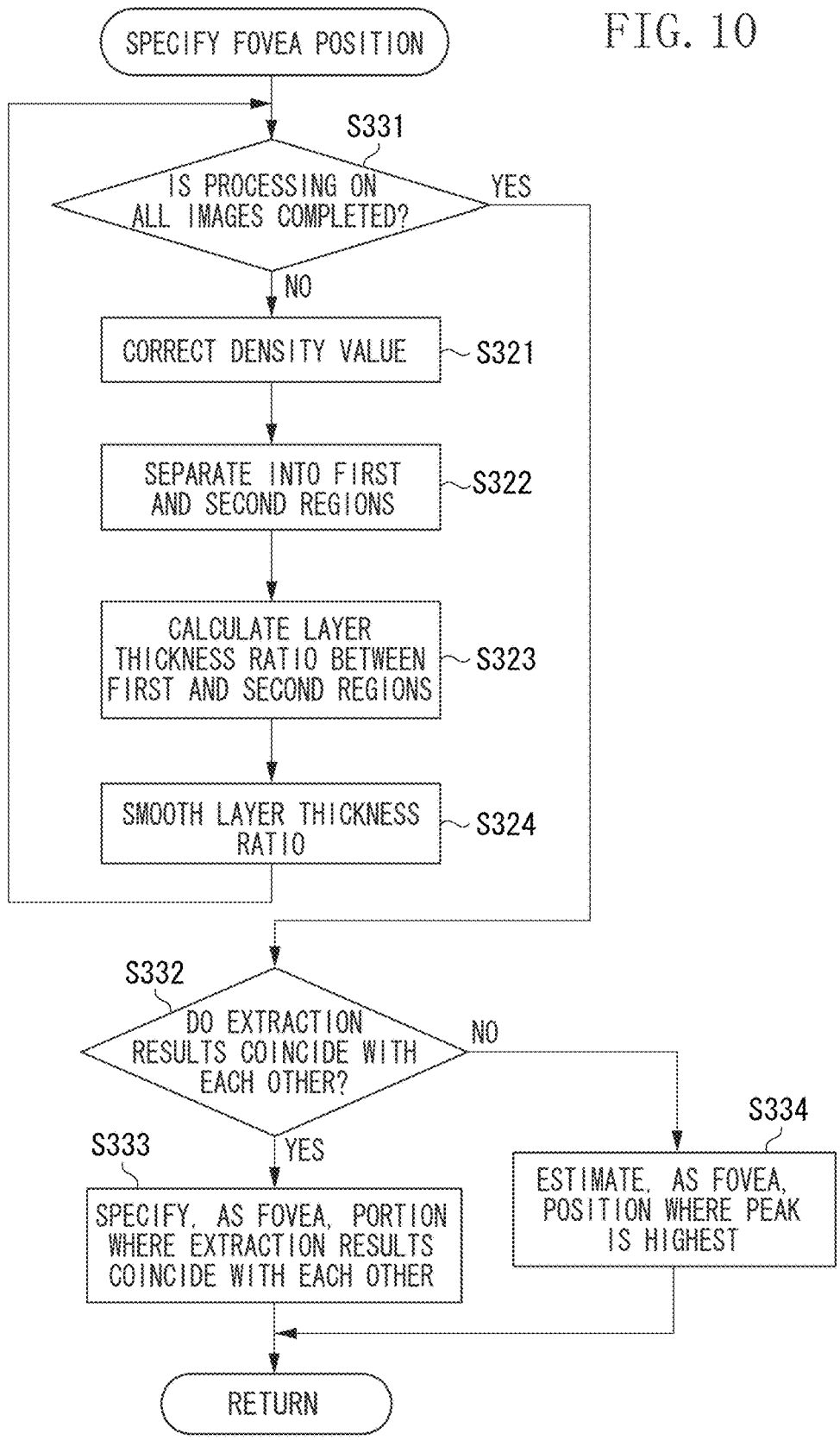
FIG. 10 is a flowchart illustrating an example of a procedure for estimating the fovea position.

In the first to third exemplary embodiments, a method for specifying the fovea position from a single tomographic image is illustrated. In a fourth exemplary embodiment, a method for specifying the fovea position from a plurality of tomographic images is illustrated. To acquire detailed information of a subject's eye, the OCT 100 often has a plurality of scanning modes. Specifically, in addition to a line scan, such as a vertical scan or a horizontal scan, for scanning the same part once each time, there are a radial scan for radially scanning the same part, and a cross scan for scanning in directions orthogonal to each other. In the present exemplary embodiment, a description is given of an example of a case where a cross scan is performed on a macular portion. FIG. 10 is a flowchart illustrating an example of the procedure of a fovea position estimation process according to the present exemplary embodiment. The processes of steps S321 to S324 are similar to those in the first exemplary embodiment and therefore are not described in detail here. Tomographic images obtained by a cross scan correspond to examples of a plurality of tomographic images obtained by scanning the fundus with measurement light in directions different from each other (directions orthogonal to each other).

In step S331, the estimation unit 204 determines whether the fovea positions are estimated from all the tomographic images. If there is a tomographic image from which the fovea position has not yet been estimated (NO in step S331), the processing proceeds to step S321. In step S321, the estimation of the fovea position illustrated in the first exemplary embodiment is executed. If, on the other hand, the fovea positions are estimated from all the tomographic images (YES in step S331), the processing proceeds to step S332. In step S332, the estimation unit 204 compares the fovea positions estimated in the respective tomographic images. In a case where the position of the fovea is estimated from a single tomographic image, it is difficult to confirm whether the estimated position is a truly correct position. The use of a plurality of B-scan images, however, can improve the accuracy of the estimation of the position of the fovea. Thus, the estimation unit 204 compares the results of estimating the fovea positions in the respective tomographic images. Then, if the estimated positions of the fovea in the respective tomographic images coincide with each other (YES in step S332), the processing proceeds to step S333. In step S333, the estimation unit 204 estimates as the fovea position the point at which the estimated positions of the fovea in the respective tomographic images coincide with each other. That is, the estimation unit 204 estimates the position of the fovea based on the result of comparison of the layer thicknesses in the plurality of respective tomographic images. More specifically, the estimation unit 204 estimates the position of the fovea from each of the plurality of tomographic images obtained by the acquisition unit 201 scanning different positions in the fundus with measurement light.

If, on the other hand, the estimated positions of the fovea in the respective tomographic images do not coincide with each other (NO in step S332), the processing proceeds to step S334. In step S334, the estimation unit 204 estimates as the fovea the position where the peak of the smoothed layer thickness ratio calculated in step S325 is the highest among the plurality of tomographic images.

Before comparing the estimated positions of the fovea, the estimation unit 204 may detect, using a known technique, the movement of the eye from a fundus image obtained by scanning laser ophthalmoscopy (SLO) and perform registration on the tomographic images based on the detected movement. Registration is performed on the tomographic images, whereby it is possible to compare the estimated positions of the fovea more accurately.

According to the present exemplary embodiment, it is possible to estimate the fovea position with higher accuracy than a case where the fovea position is estimated from a single B-scan image. In the present exemplary embodiment, a method for, in a case where the fovea positions estimated from a plurality of B-scan images do not coincide with each other, analyzing the peak of the smoothed layer thickness ratio is used. The present exemplary embodiment, however, is not limited to this. Alternatively, for example, similarly to the above method, the center of each B-scan image may be estimated as the fovea. Yet alternatively, the fovea position may be estimated based on imaging information. Yet alternatively, if the estimated positions of the fovea in the respective tomographic images do not coincide with each other, it may be determined that the fovea position cannot be estimated, and the display control unit 205 may cause the display unit 206 to display a message that the fovea position cannot be estimated. In this manner, it is possible to notify the operator of only a highly accurate fovea position. Thus, it is possible to reduce the possibility that incorrect information is delivered to the operator.

Also in B-scan images obtained by a multi-cross scan for scanning a plurality of lines orthogonal to each other, the fovea position can be specified using a similar method. A plurality of B-scan images obtained by a multi-cross scan are used as analysis targets, whereby the accuracy of the specifying the fovea position is improved. At the same time, however, the processing time may increase. In this case, as illustrated in the first exemplary embodiment, if it is possible to determine from imaging information that a fovea region is clearly not included in a B-scan image, the B-scan image is not used as an analysis target. Then, only an image that can be determined as including a fovea region is analyzed using the above method. Consequently, it is possible to both improve the accuracy of the specifying of the fovea position and improve the processing speed.

In the fourth exemplary embodiment, a method in a case where the fovea position is specified from a plurality of B-scan images is illustrated. Alternatively, another method may be used. Specifically, in a ninth variation example, the OCT 100 is used, whereby it is possible to generate a three-dimensional tomographic image of a subject's eye by scanning a rectangular region in the retina multiple times in the horizontal direction while moving the acquisition position. That is, the acquisition unit 201 acquires a three-dimensional tomographic image. The three-dimensional tomographic image includes a plurality of B-scan images.

The estimation unit 204 executes processing similar to that according to the first exemplary embodiment on the acquired three-dimensional tomographic image. Thus, it is possible to associate the estimated position of the fovea with the three-dimensional tomographic image. Further, the three-dimensional tomographic image is integrated in the depth direction, whereby it is possible to generate an integrated image representing the surface of the fundus. Thus, it is also possible to associate the estimated position of the fovea with the integrated image. Further, since an SLO image, a fundus image acquired by the fundus camera, and the integrated image are two-dimensional images representing the same surface of the fundus, registration is performed on these images, whereby it is also possible to associate the estimated position of the fovea with respect to the SLO image and the fundus image.

The display control unit 205 can cause the display unit 206 to display the front image 110 and display the estimated fovea position on the front image 110 displayed based on the above association. As the front image 110, the SLO image or the integrated image obtained by integrating the acquired three-dimensional tomographic image of the subject's eye in the Z-axis direction can be displayed. Alternatively, the display unit 206 can display as the front image 110 an en face image obtained by projecting the three-dimensional tomographic image on a plane based on any two reference surfaces, or the fundus image captured by the fundus camera.

According to the present variation example, it is possible to display the fovea position on a front image obtained by observing a subject's eye from the front. Thus, the operator can easily recognize the fovea position on a surface of the fundus.

In a fifth exemplary embodiment, an image of a portion around the estimated fovea position is analyzed in detail to detect retinal detachment in the fovea. A cell present in the RPE ingests the photoreceptor cell outer segment. Thus, in a healthy eye, the photoreceptor cell outer segment and the RPE are observed being close to each other. However, in an eye in which retinal detachment occurs, the photoreceptor cell outer segment and the RPE are observed being separate from each other. As described above, the fovea is a part having great influence on the visual performance. Thus, it is desirable that in a case where retinal detachment occurs around the fovea, the retinal detachment should be able to be detected in its early stages even if occurring in a small region. It is difficult to detect such small retinal detachment from the entirety of a tomographic image due to the influence of noise in the image. In response, an image processing apparatus according to the present exemplary embodiment limits a target range of image analysis using the fovea position estimated by the methods described in the first to fourth exemplary embodiments and performs a detailed analysis process.

Figure 11:
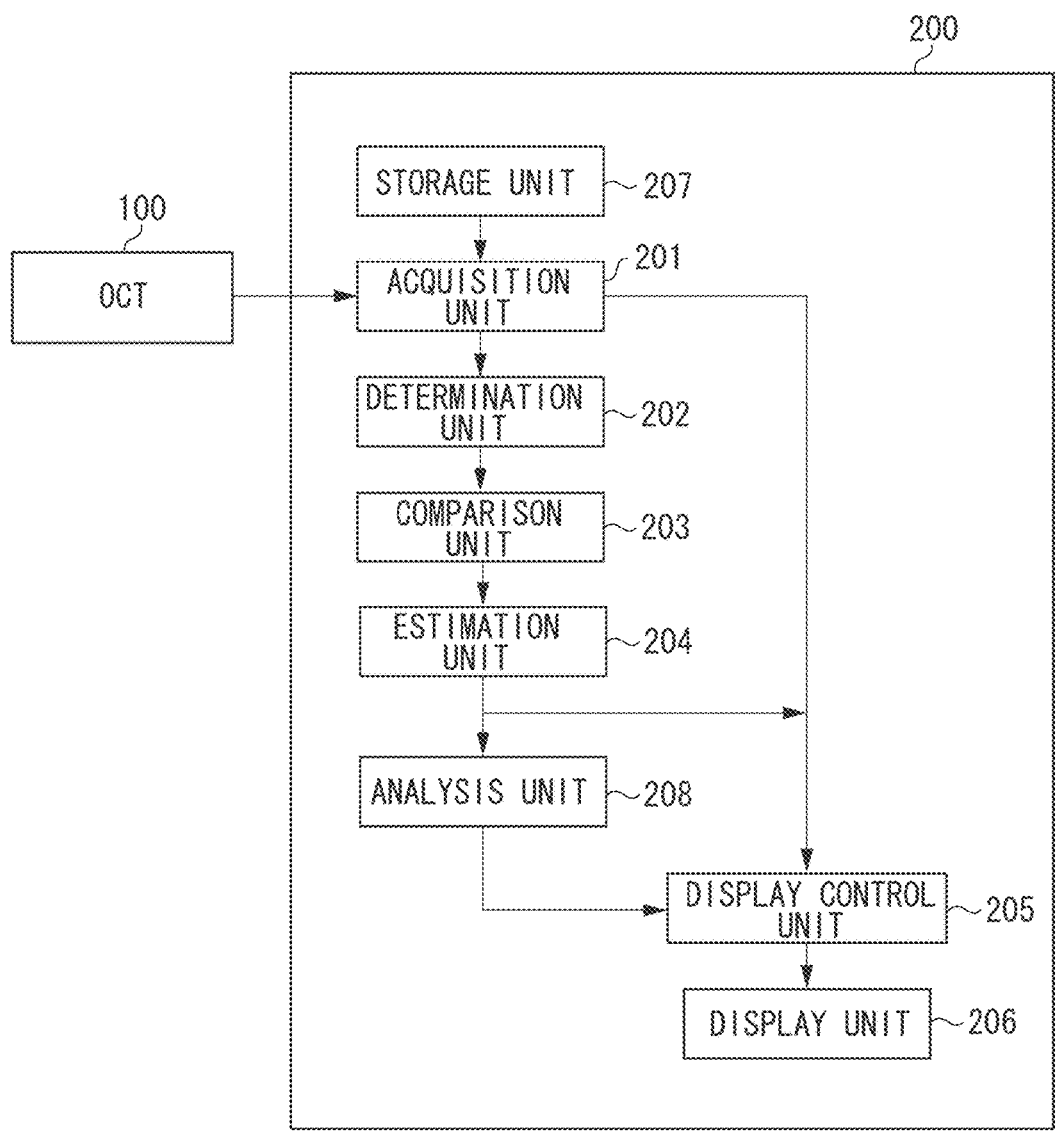
FIG. 11 is a diagram illustrating an example of a configuration of a system.

A system illustrated in FIG. 11 is almost similar to the system in FIG. 1. The system in FIG. 11, however, is different from the system in FIG. 1 in that an analysis unit 208 is included.

Figure 12:
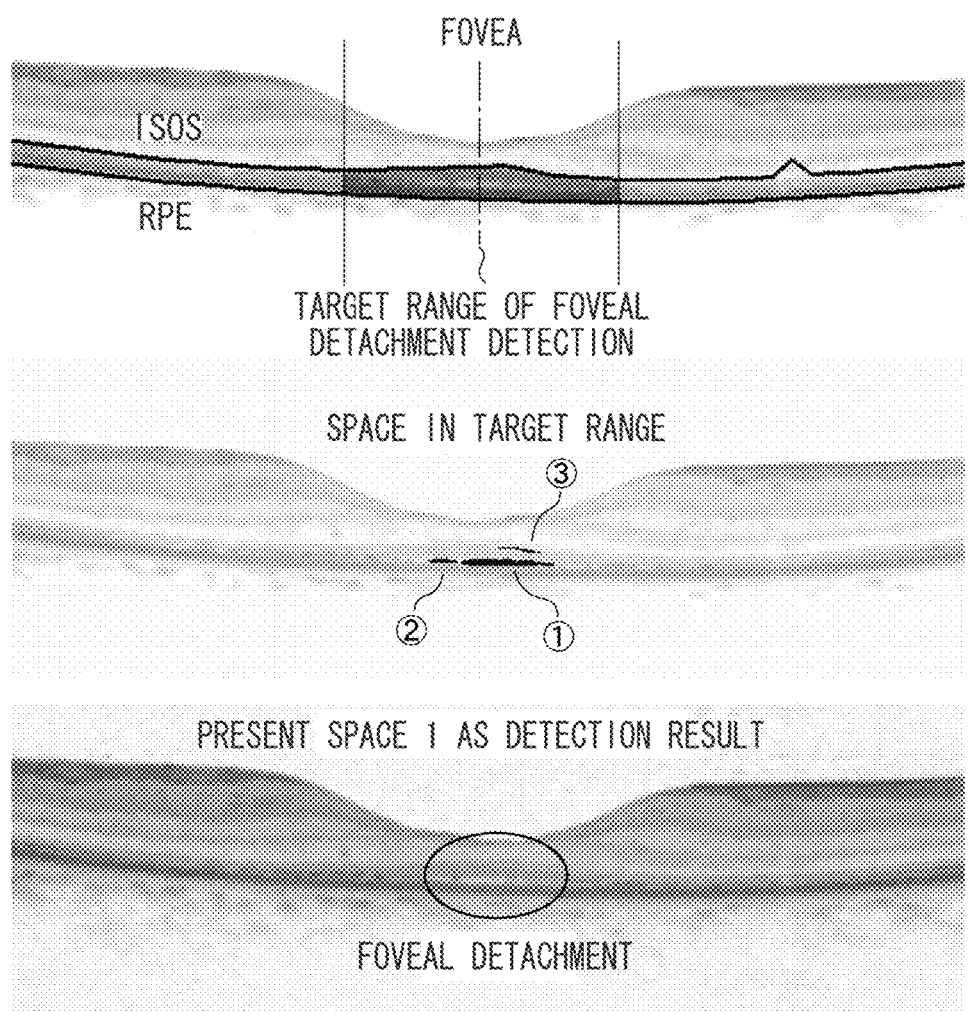
FIG. 12 is a diagram illustrating an example of a method for detecting retinal detachment.

Similarly to the acquisition unit 201 and the like, the CPU of the image processing apparatus 200 functions as the analysis unit 208. The analysis unit 208 analyzes a tomographic image to detect an abnormal part. For example, the analysis unit 208 detects retinal detachment in the fovea. More specifically, as illustrated in FIG. 12, the analysis unit 208 determines as a target range of image analysis a region that is sandwiched between the RPE and the IS/OS junction extracted by the determination unit 202 and is near the position of the fovea estimated by the estimation unit 204. Then, the analysis unit 208 analyzes the density or the luminance of an image in this target range to detect retinal detachment.

Figure 13B:
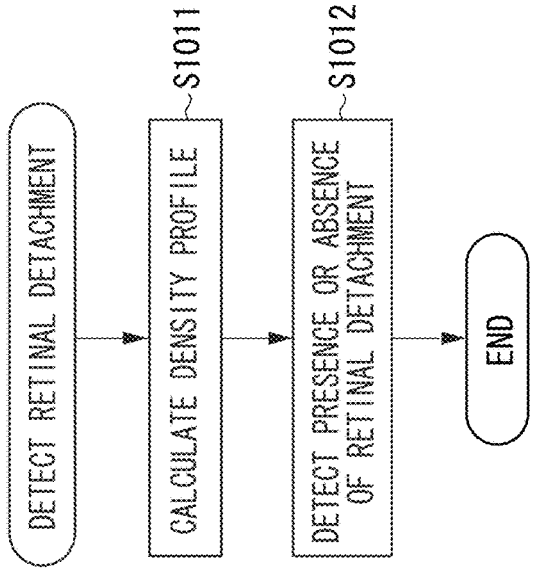
FIGS. 13A and 13B are flowcharts illustrating an example of a procedure for detecting retinal detachment.
Figure 13A:
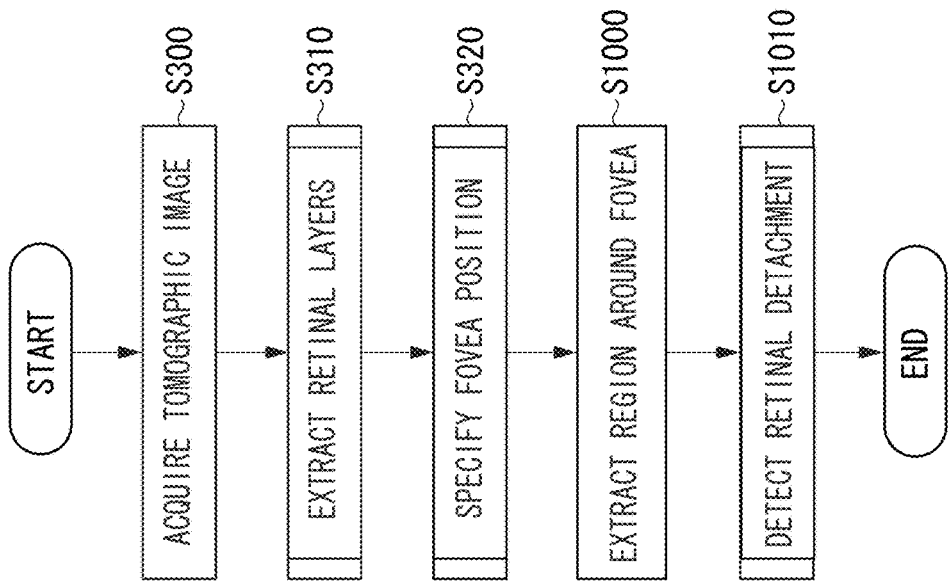

FIGS. 13A and 13B are flowcharts illustrating an example of an operation of the image processing apparatus according to the present exemplary embodiment. FIG. 13A is a flowchart illustrating an example of the general operation of the image processing apparatus according to the present exemplary embodiment. Steps S300 to S320 are similar to steps S300 to S320 illustrated in FIG. 2A and therefore are not described in detail here.

In step S1000, the analysis unit 208 extracts a target range of image analysis including about several tens of pixels to a hundred pixels to the left and right of the position of the fovea estimated by the estimation unit 204. The upper end and the lower end of this target range are defined by the IS/OS junction and the RPE extracted in step S315. That is, the analysis unit 208 corresponds to an example of an extraction unit configured to, based on the position of the fovea estimated by an estimation unit, extract a partial region included in the tomographic image and including the position of the fovea.

Next, in step S1010, the analysis unit 208 analyzes the target range of the tomographic image to detect retinal detachment. FIG. 13B is a flowchart illustrating an example of the detailed processing procedure of step S1010.

First, in step S1011, in the extracted target range, the analysis unit 208 scans the image in the Z-axis direction and calculates a density profile or a luminance profile.

In step S1012, if a low-density region having a certain width is continuously present in the X-axis direction between the IS/OS junction and the RPE in the density profile, the analysis unit 208 determines that there is a possibility that retinal detachment occurs. That is, the analysis unit 208 corresponds to an example of a detection unit configured to detect retinal detachment based on a change in the density or the luminance, along a depth direction, of the region extracted by the extraction unit.

Figure 14A:
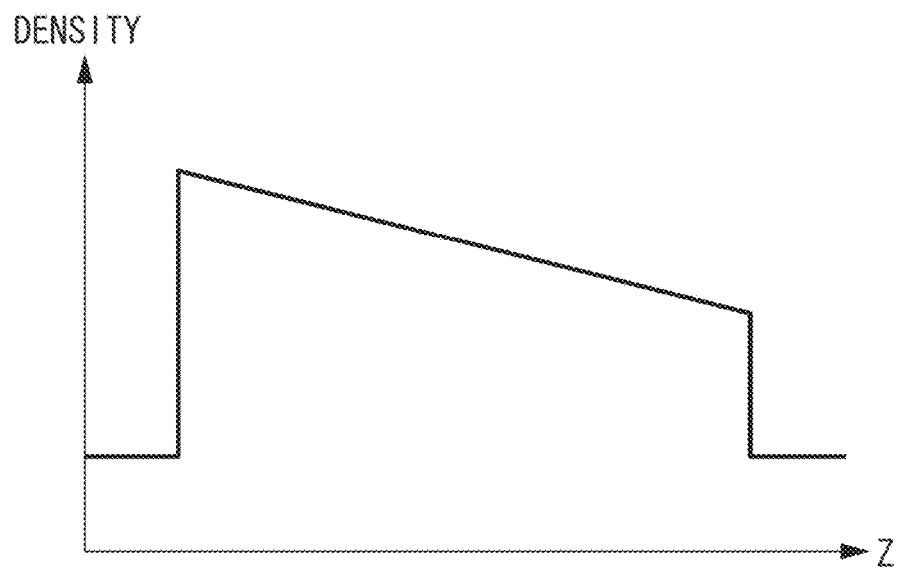
FIGS. 14A and 14B are diagrams illustrating examples of a density profile.
Figure 14B:
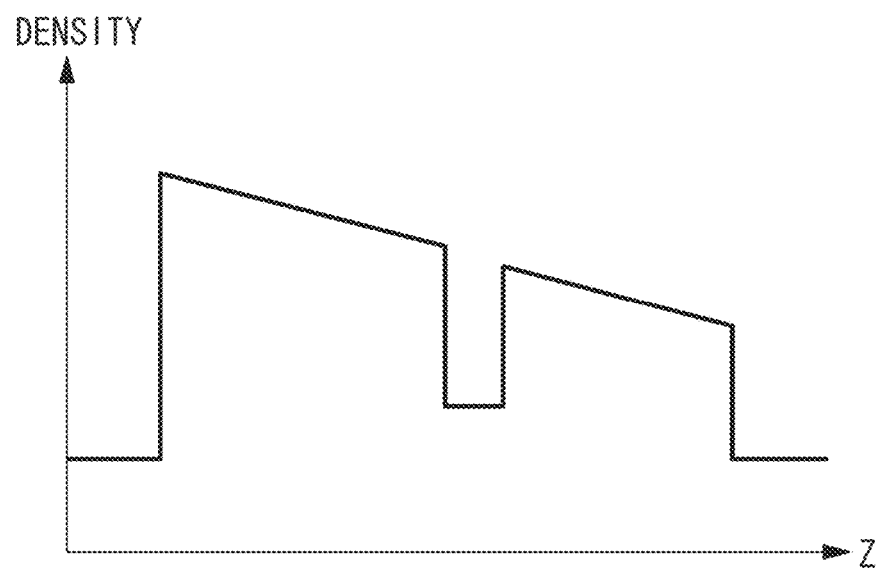

If retinal detachment is not present in the fovea, then as illustrated in FIG. 14A, the density generally continuously changes from the IS/OS junction to the RPE. If, on the other hand, retinal detachment is present, then as illustrated in FIG. 14B, a retinal detachment region is visualized as a region (a low-density region) where the density decreases by a predetermined threshold or more as compared with other regions. Thus, a low-density region is present between high-density regions. Thus, between the IS/OS junction and the RPE, the analysis unit 208 determines whether a low-density region sandwiched between high-density regions is present, and can detect the presence or absence of retinal detachment. Specifically, between the IS/OS junction and the RPE, the analysis unit 208 detects as a retinal detachment region a region where the density decreases by a predetermined threshold or more as compared with the densities of regions near this region as illustrated in FIG. 14B.

Figure 15:
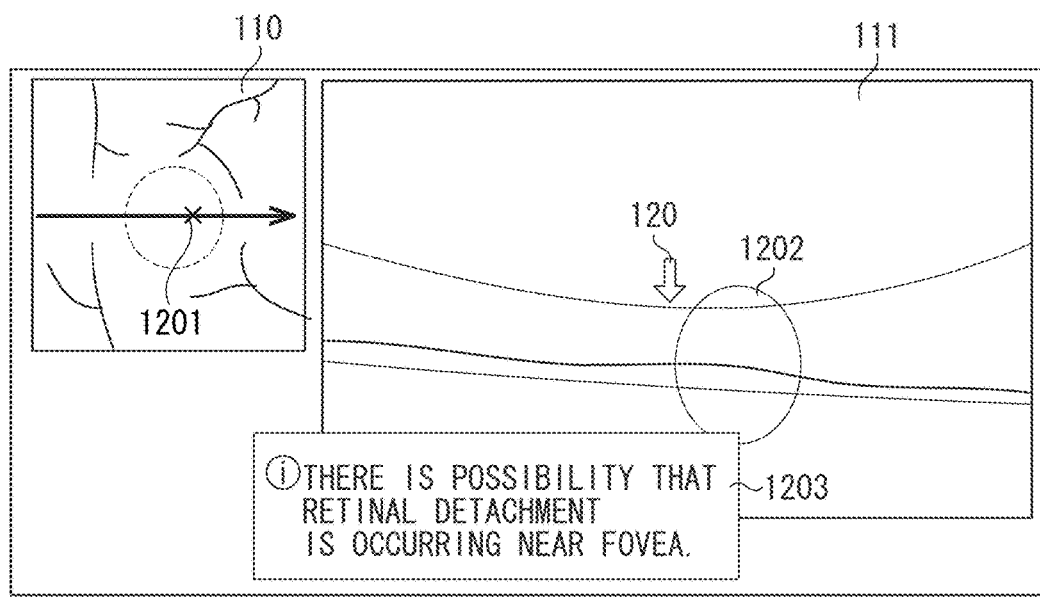
FIG. 15 is a diagram illustrating an example of a display screen.

The display control unit 205 causes the display unit 206 to display the result of the analysis by the analysis unit 208. FIG. 15 is a diagram illustrating an example of display of the display unit 206. The display control unit 205 causes the display unit 206 to display a tomographic image 111, which is acquired by the acquisition unit 201, a marker 120, which indicates the position of the fovea estimated by the estimation unit 204, and the result of the analysis by the analysis unit 208. The display control unit 205 may cause the display unit 206 to display, as an example of the analysis result to be displayed, a marker 1202, which surrounds the retinal detachment region, or a message 1203, which indicates the presence or absence of retinal detachment. The marker 1202 surrounding the retinal detachment region functions as a marker indicating the retinal detachment region.

The display control unit 205 may be configured to, if the analysis unit 208 detects retinal detachment, cause the display unit 206 to automatically display a tomographic image obtained by enlarging a portion around the fovea. The tomographic image obtained by enlarging the portion around the fovea may be superimposed on the tomographic image 111, or may be displayed to be switchable with the tomographic image 111. Further, the display control unit 205 may cause the display unit 206 to display a marker 1201, which indicates the detected retinal detachment region, on the front image 110.

According to the present exemplary embodiment, it is possible to accurately detect retinal detachment in the fovea. Further, the region of the retinal detachment is clearly indicated on a tomographic image or a front image. Thus, a doctor can easily understand the region where the retinal detachment occurs.

In a tenth variation example, a discrimination analysis method is used to detect retinal detachment. For example, the analysis unit 208 determines a threshold by applying the discrimination analysis method not to the entirety of the tomographic image but only to a target range of image analysis extracted based on the estimated fovea. Then, the analysis unit 208 binarizes pixels in the target range using the determined threshold. By this binarization, the analysis unit 208 divides the pixels in the target range into a high-density region and a low-density region. The analysis unit 208 extracts the low-density region after the binarization. In FIG. 12, the analysis unit 208 extracts regions 1 to 3, for example, as low-density regions. Then, the analysis unit 208 selects a region of the largest size from among the low-density regions 1 to 3 and determines, based on at least one of the size, the shape, and the position of the selected low-density region, whether retinal detachment occurs. For example, in FIG. 12, the analysis unit 208 selects the low-density region 1. Then, the analysis unit 208 determines whether the size, the shape, or the position of this region contradicts the symptoms of retinal detachment. The analysis unit 208 determines whether the size of the low-density region 1, for example, is equal to or greater than a predetermined threshold, or whether the length in the Z-axis direction of the low-density region 1 is greater than the length in the X-direction of the low-density region 1, or whether the position of the low-density region 1 is within a predetermined distance from the RPE.

Then, if the analysis unit 208 determines that the low-density region 1 is retinal detachment, then as illustrated in FIG. 12, the display control unit 205 causes the display unit 206 to display information indicating the position of the retinal detachment on the tomographic image. The display control unit 205 may cause the display unit 206 to highlight the low-density region 1. As an example of the highlighting, the low-density region determined as retinal detachment may be displayed in a color different from that of the tomographic image, or the contour of the low-density region may be indicated.

According to the present variation, it is possible to achieve an effect similar to that of the fifth exemplary embodiment.

In the fifth exemplary embodiment, as the processing of the analysis unit 208, the process of analyzing the presence or absence of retinal detachment is illustrated. In a sixth exemplary embodiment, another process is illustrated. That is, the estimated position of the fovea can also be used for a process other than the process of detecting retinal detachment.

Figure 16:
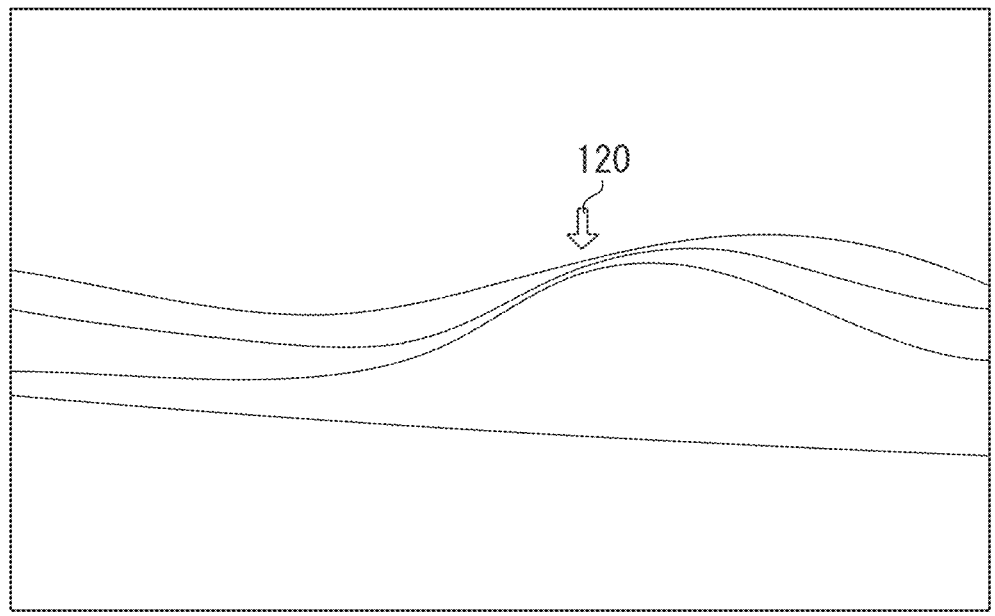
FIG. 16 is a diagram illustrating an example of a tomographic image.

As described above, the fovea in a healthy eye is observed as a depressed region on a tomographic image. Further, it is known that the thicknesses of the retinal layers are almost symmetrical in the up-down direction with respect to a straight line connecting the optic disc and the macula, and the thicknesses of the layers outside the RNFL are almost symmetrical also in the left-right direction with respect to the straight line connecting the optic disc and the macula. On the other hand, if macular edema occurs, for example, as illustrated in FIG. 16, a macular portion may protrude, and the symmetry of the layer thicknesses may not be maintained. In response, after the fovea position is specified using the above method, the thicknesses of the retinal layers are further analyzed in the X-axis direction, whereby it is possible to detect the abnormality of a portion around the fovea. Specifically, for example, the analysis unit 208 analyzes the layer thickness of a predetermined layer around the fovea and determines whether the symmetry of the layer thickness of the predetermined layer with respect to the fovea is maintained. If the symmetry is not maintained, the analysis unit 208 determines that the portion around the fovea is abnormal. Then, using a method similar to that according to the fifth exemplary embodiment, the display unit 206 displays a message that the symmetry is not maintained, notifying the operator of the determination result. Layer thickness information used for the determination may be newly calculated, or the layer thicknesses calculated in step S320 may be used.

According to the present exemplary embodiment, based on the estimated position of the fovea, it is possible to detect the abnormality of an eye. Further, it is possible to notify the operator that an abnormality is detected. Thus, the operator can easily know that there is an abnormality.

In the first exemplary embodiment, the estimation unit 204 estimates the position of the fovea using the thickness of the first region and the thickness of the second region. Alternatively, the estimation unit 204 may estimate the position of the fovea based only on either one of the thickness of the first region and the thickness of the second region.

For example, in a seventh exemplary embodiment, based on distribution of the thickness of the first region in the X-axis direction obtained by the determination unit 202 in step S322, the estimation unit 204 extracts a position in the tomographic image where the thickness of the first region is at a local minimum and/or a minimum. Then, the estimation unit 204 estimates the extracted position as the position of the fovea. That is, the estimation unit 204 estimates the position of the fovea based on the distribution of the thickness of only at least a partial region from the ILM to the boundary between the external plexiform layer and the external granular layer included in the tomographic image. More specifically, the estimation unit 204 estimates the position of the fovea based on an extreme point of the thickness of the first region.

Alternatively, the estimation unit 204 may extract a position in the tomographic image where the thickness of the second region obtained by the determination unit 202 in step S322 is at a local maximum and/or at a maximum. Then, the estimation unit 204 may estimate the extracted position as the position of the fovea. That is, according to the present exemplary embodiment, the estimation unit 204 can achieve an effect similar to that of the first exemplary embodiment. Further, to estimate the position of the fovea, the determination unit 202 only needs to calculate the thickness of one of the first and second regions. Thus, it is possible to shorten the processing time.

Figure 17:
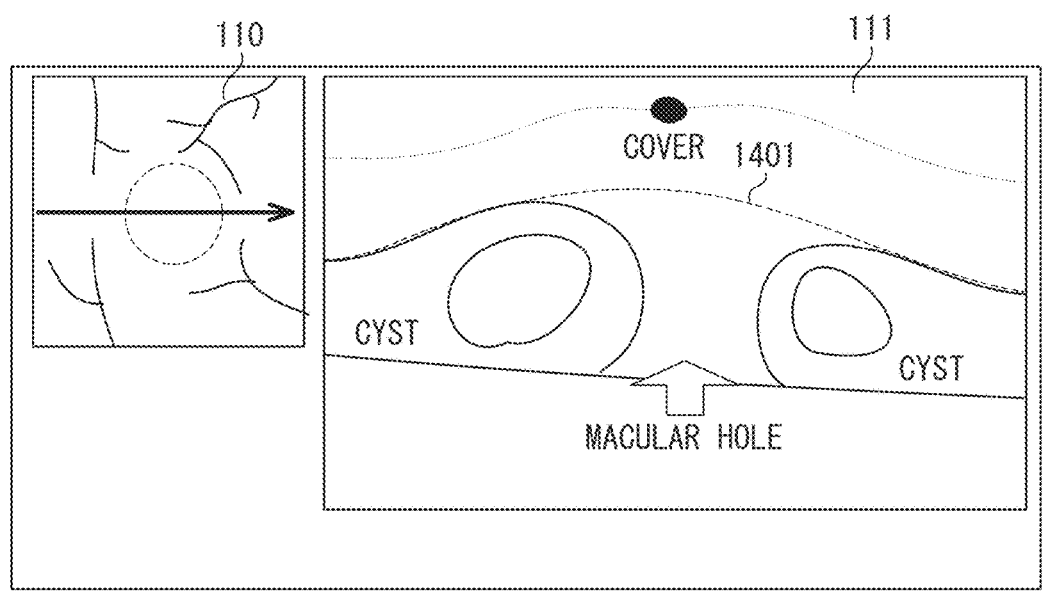
FIG. 17 is a diagram illustrating an example of a display screen.

In an eighth exemplary embodiment, a method for displaying the result of the analysis by the analysis unit 208 is illustrated taking a tomographic image of a macular hole as an example. Generally, a portion anterior to the retina in an eyeball is filled with the vitreous body, which contains water, collagen fibers, and hyaluronic acid as main components. The vitreous body shrinks with age and detaches from the retina. In this process, as a result of radially pulling the retina near the fovea, a hole may occur. This hole is termed a macular hole. A tomographic image including a macular portion represents a shape in which, for example, as illustrated in FIG. 17, the ILM is divided. If a macular hole occurs, the eyesight decreases, and the center field of vision becomes difficult to view. The more time passes from the appearance of the macular hole, the more difficult the treatment becomes. Thus, it is desirable to detect a macular hole in its early stages.

The analysis unit 208 of this image processing apparatus analyzes a portion around the ILM extracted in step S310. Since retinal layers are extracted using snakes as an algorithm of the active contour method in step S315, an ILM extraction result 1401 is a single line as illustrated in FIG. 17 also in a tomographic image in which a macular hole occurs. Thus, the analysis unit 208 determines whether the ILM extraction result 1401 runs through the background regions determined in step S310, and can determine whether a macular hole is present. That is, if determining that the ILM near the fovea runs through the background regions, the analysis unit 208 determines that a macular hole is present. Further, there is a case where a high-density region is present above the ILM (on the anterior eye segment side in the Z-direction) in the tomographic image. This high-density region is the posterior vitreous cortex, a cover, or a valve, except for the influence of noise. In a case where a high-density region is present immediately above the macular hole, the analysis unit 208 can determine that the high-density region is a cover or a valve. In other cases, the analysis unit 208 can determine that the high-density region is the posterior vitreous cortex. That is, if detecting a macular hole, the analysis unit 208 detects a cover or a valve based on the macular hole.

Further, the analysis unit 208 may detect a cyst from the tomographic image. Specifically, if a circular or elliptical low-density region is present in a region between the ILM and the RPE detected in step S315, the analysis unit 208 determines that this low-density region is a cyst. That is, the analysis unit 208 corresponds to an example of a detection unit configured to perform structure analysis on the tomographic image to detect an abnormal part of a subject's eye.

Figure 18:
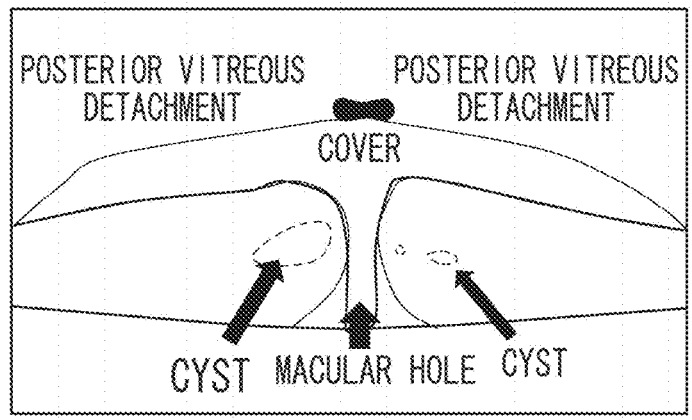
FIG. 18 is a diagram illustrating an example of a display screen.

As illustrated in FIG. 17, the display control unit 205 causes the display unit 206 to display findings such as the macular hole, the cover, and the cyst detected by the analysis unit 208 in association with the positions in the tomographic image where the findings are detected. The closer to the fovea the part where the finding is detected, the more likely the finding influences the eyesight. Thus, the display control unit 205 may cause the display unit 206 to display the findings such that the closer to the position of the fovea estimated by the estimation unit 204, the more emphatically the finding is displayed on the display unit 206. For example, even in a case where a plurality of findings indicating cysts, which are of the same type, are detected, the display control unit 205 may cause the display unit 206 to display characters indicating the cysts such that the characters indicating a cyst close to the fovea are larger than the characters indicating a cyst far from the fovea. FIG. 18 illustrates a display screen in a case where a cyst on the left of the figure is closer to the fovea than a cyst on the right of the figure is, and therefore, the characters of the cysts are displayed such that the characters of the cyst on the left are larger. Alternatively, a finding close to the fovea may be emphasized by varying not the size of the characters but the color of the characters. That is, based on the position of the fovea, the display control unit 205 changes the display form of the characters of a finding to be displayed on the display unit 206. To simplify FIG. 17, the marker 120 indicating the position of the fovea is omitted in FIG. 17. That is, the marker 120 indicating the position of the fovea may be displayed simultaneously with the findings on the display unit 206.

According to the present exemplary embodiment, it is possible to emphatically display a finding according to the distance from the fovea. Thus, the operator can easily understand an important finding among a plurality of findings.

Figure 19:
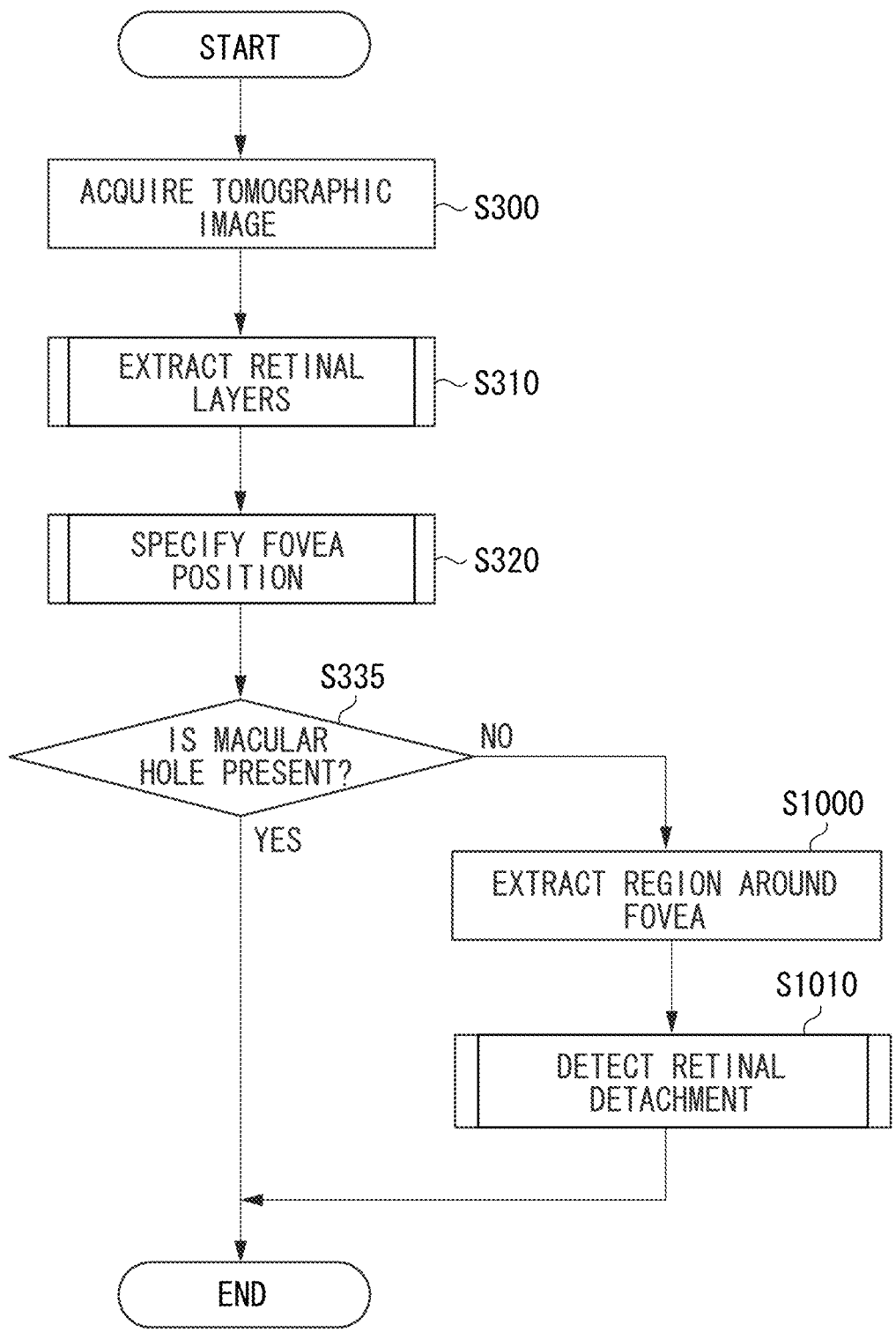
FIG. 19 is a flowchart illustrating an example of a procedure for detecting retinal detachment.

In a ninth exemplary embodiment, with reference to FIG. 19, a description is given of an example of the process of analyzing retinal detachment around the fovea and another finding. The processes of steps S300 to S320 and steps S1000 and S1010 in FIG. 19 are similar to those of steps S300 to S320 and steps S1000 and S1010 in the above exemplary embodiments and therefore are not described in detail here.

Small retinal detachment around the fovea detected in the fifth exemplary embodiment is a finding of a primary lesion. Thus, the configuration is such that if a retinal disease that has progressed to some extent is detected, retinal detachment around the fovea is not detected.

Specifically, in step S335, for example, as illustrated in the eighth exemplary embodiment, first, the analysis unit 208 detects the presence or absence of a macular hole from the running state of the ILM extracted in step S315. Then, if a macular hole is detected (YES in step S335), the analysis unit 208 determines that steps S1000 and S1010 are not to be performed. Then, the display control unit 205 causes the display unit 206 to display a message that a macular hole is present. Then, the processing ends.

If, on the other hand, it is determined that no macular hole is present (NO in step S335), the analysis unit 208 executes the above process of detecting retinal detachment. In the present exemplary embodiment, a macular hole is used as an example. The present exemplary embodiment, however, is not limited to this. Alternatively, for example, macular edema may be detected, or an abnormal running state of the RPE due to RPE detachment may be detected. That is, if detecting a predetermined finding, the analysis unit 208 does not execute the process of detecting retinal detachment.

According to the present exemplary embodiment, it is not necessary to perform unnecessary processing. Thus, it is possible to speed up the processing of the entirety of an apparatus. Further, it is possible to prevent the apparatus from detecting small retinal detachment and obtaining an incorrect detection result even in a case where illness is progressing.

In a tenth exemplary embodiment, an example is described where a search is performed for a similar case (a similar image) using the position of the fovea estimated in the above exemplary embodiments.

In the present exemplary embodiment, the storage unit 207 stores as cases a plurality of tomographic images associated with the position of the fovea estimated by the estimation unit 204 or the position of the fovea specified by a doctor. That is, the storage unit 207 stores each of a plurality of tomographic images in association with the position of the fovea in the tomographic image.

Then, the estimation unit 204 estimates the position of the fovea from the tomographic image in step S325 and then acquires from the storage unit 207 a tomographic image associated with the position of the fovea similar to the estimated position of the fovea or having a difference within a predetermined threshold from the estimated position of the fovea. That is, the estimation unit 204 corresponds to an example of a similar image acquisition unit configured to acquire from a storage unit a tomographic image having the position of the fovea corresponding to the estimated position of the fovea.

Then, the display control unit 205 causes the display unit 206 to display the tomographic image acquired from the storage unit 207 and the tomographic image acquired by the acquisition unit 201 such that these tomographic images are next to each other. In this manner, it is possible to display a plurality of tomographic images easily comparable by the operator.

Further, the storage unit 207 may store as cases a plurality of tomographic images associated with a finding and the position of the finding detected by the analysis unit 208 in the above exemplary embodiments or a finding and the position of the finding specified by a doctor, in addition to the position of the fovea. That is, the storage unit 207 stores each of a plurality of tomographic images in association with the position of the fovea and the position of an abnormal part. At this time, the position of the finding corresponds to an example of the position of an abnormal part. Then, in this case, the estimation unit 204 estimates the position of the fovea from the tomographic image in step S325, and the analysis unit 208 detects a finding and the position of the finding. Then, the estimation unit 204 acquires from the storage unit 207 a tomographic image having a positional relationship between the fovea and the finding that is similar to the positional relationship between the estimated fovea and the detected finding or has a difference within a predetermined threshold from the positional relationship between the estimated fovea and the detected finding. That is, the estimation unit 204 acquires from the storage unit 207 a tomographic image having a relationship between the position of the fovea and the position of an abnormal part that corresponds to the relationship between the estimated position of the fovea and the detected position of the abnormal part.

Then, the display control unit 205 causes the display unit 206 to display the tomographic image acquired from the storage unit 207 and the tomographic image acquired by the acquisition unit 201 such that these tomographic images are next to each other. It is desirable that the estimation unit 204 should acquire from the storage unit 207 a tomographic image including a finding of the same type as a finding in the tomographic image as the processing target. That is, the estimation unit 204 acquires from the storage unit 207 a tomographic image having a relationship between the position of the fovea and the position of a finding that is the closest possible to the relationship between the position of the fovea and the position of the finding in the tomographic image as the processing target. In this manner, it is possible to display a plurality of tomographic images easily comparable by the operator.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-007429, filed Jan. 18, 2016, which is hereby incorporated by reference herein in its entirety.

What is claimed is:

1. An image processing apparatus comprising:
at least one memory that stores at least one program of instructions; and
at least one processor that is coupled to the at least one memory and that executes the at least one program of instructions to implement:
a layer boundary detection unit configured to detect a plurality of layer boundaries included in a tomographic image of a fundus of a subject's eye captured by an optical coherence tomography (OCT) optical device;
a determination unit configured to determine a first region where a density or a luminance of a pixel included in the tomographic image is equal to or greater than a threshold and a second region where a density or a luminance of a pixel is less than the threshold by analyzing the tomographic image, the first region including at least a partial region of a region from an internal limiting membrane to a boundary between an external plexiform layer and an external granular layer, the second region including at least a partial region of a region from the boundary to a photoreceptor cell inner segment/outer segment junction;
a comparison unit configured to compare a thickness of the first region with a thickness of the second region in a depth direction of the tomographic image; and
an estimation unit configured to estimate a position of a fovea of the fundus based on a result of the comparison by the comparison unit.

2. The image processing apparatus according to claim 1, wherein the determination unit determines the first and second regions based on a layer boundary detected from the tomographic image.

3. The image processing apparatus according to claim 1, wherein the comparison unit outputs, as the result of the comparison, a difference between the thickness of the first region and the thickness of the second region.

4. The image processing apparatus according to claim 1, wherein the comparison unit outputs, as the result of the comparison, a value indicating a ratio between a thickness of the first region and a thickness of the second region, or a ratio between the thickness of the first region or the thickness of the second region and a sum of the thicknesses of the first and second regions.

5. The image processing apparatus according to claim 1, wherein the first and second regions are included in a range from the internal limiting membrane to the photoreceptor cell inner segment/outer segment junction.

6. The image processing apparatus according to claim 1, wherein the comparison unit is configured to compare a thickness of the first region with a thickness of the second region in a direction orthogonal to the depth direction at a plurality of positions, and further comprises a calculation unit configured to calculate a moving average of results of the comparisons of the plurality of positions by the comparison unit, and
wherein the estimation unit estimates the position of the fovea based on the moving average calculated by the calculation unit.

7. The image processing apparatus according to claim 1, wherein in a case where the position of the fovea cannot be estimated based on the result of the comparison by the comparison unit, the estimation unit estimates a center of the tomographic image as the position of the fovea.

8. The image processing apparatus according to claim 1, wherein the estimation unit estimates the fovea based on the layer boundary detected, and in a case where the fovea cannot be estimated based on the layer boundary detected by the detection unit, the estimation unit estimates the fovea based on the result of the comparison by the comparison unit.

9. The image processing apparatus according to claim 1, wherein the estimation unit estimates the fovea based on an integrated value of a luminance of the tomographic image in the depth direction or a density of the tomographic image in the depth direction, and in a case where the fovea cannot be estimated based on the integrated value, the estimation unit estimates the fovea based on the result of the comparison by the comparison unit.

10. The image processing apparatus according to claim 1, wherein in a case where the position of the fovea cannot be estimated based on the result of the comparison by the comparison unit, the estimation unit estimates the position of the fovea based on information regarding a presentation position of a fixation lamp.

11. The image processing apparatus according to claim 1, wherein based on information regarding a presentation position of a fixation lamp, the estimation unit determines whether the position of the fovea is to be estimated.

12. The image processing apparatus according to claim 1, wherein the estimation unit estimates the fovea based on information regarding a presentation position of a fixation lamp and the result of the comparison by the comparison unit.

13. The image processing apparatus according to claim 1, further comprising:
a tomographic image acquisition unit configured to acquire a plurality of tomographic images obtained by scanning the fundus with measurement light in a plurality of distinct directions, and
wherein the estimation unit estimates the position of the fovea based on results of comparisons by the comparison unit in each of the plurality of tomographic images.

14. The image processing apparatus according to claim 1, further comprising:
a tomographic image acquisition unit configured to acquire a plurality of tomographic images obtained by scanning positions different from each other in the fundus with measurement light, and
wherein the estimation unit estimates the position of the fovea from each of the plurality of tomographic images.

15. The image processing apparatus according to claim 1, further comprising a display control unit configured to cause a display unit to display information indicating the position of the fovea estimated by the estimation unit on the tomographic image in a superimposed manner.

16. The image processing apparatus according to claim 1, further comprising:
an extraction unit configured to, based on the position of the fovea estimated by the estimation unit, extract a partial region, in the tomographic image, including the position of the fovea; and
a detection unit configured to detect retinal detachment based on a change in a density or a luminance, along the depth direction, of the partial region extracted by the extraction unit.

17. The image processing apparatus according to claim 1, wherein a degree of abnormality of the fovea is determined based on at least one of the thickness of the first region and the thickness of the second region.

18. The image processing apparatus according to claim 1, further comprising:
a storage unit configured to store each of a plurality of tomographic images in association with a position of a fovea in a corresponding tomographic image; and
a similar image acquisition unit configured to acquire from the storage unit a tomographic image having a position of a fovea corresponding to the position of the fovea estimated by the estimation unit.

19. The image processing apparatus according to claim 1, wherein the estimation unit estimates the position of the fovea based on an extreme point of a value indicated by the result of the comparison in the tomographic image.

20. The image processing apparatus according to claim 1, wherein the estimation unit estimates, as the position of the fovea, a portion indicating that the thickness of the first region relative to the thickness of the second region is the smallest in the tomographic image.

21. The image processing apparatus according to claim 1, wherein the determination unit determines the threshold using a discrimination analysis method.

22. The image processing apparatus according to claim 8, wherein the estimation unit estimates the fovea based on a shape of the internal limiting membrane.

23. The image processing apparatus according to claim 13, wherein the distinct directions different from each other are orthogonal to each other.

24. The image processing apparatus according to claim 1, further comprising a display control unit configured to cause a display unit to display information indicating the position of the fovea estimated by the estimation unit on a front image of the fundus in a superimposed manner.

25. The image processing apparatus according to claim 18, further comprising an abnormal part detection unit configured to detect an abnormal part of a subject's eye by performing structure analysis on the tomographic image,
wherein the storage unit stores each of a plurality of tomographic images in association with a position of a fovea and a position of an abnormal part, and wherein the similar image acquisition unit acquires from the storage unit a tomographic image having a relationship between a position of a fovea and a position of an abnormal part that corresponds to a relationship between the position of the fovea estimated by the estimation unit and a position of the abnormal part detected by the detection unit.

26. An estimation method for estimating a fovea, the estimation method comprising:

detecting a plurality of layer boundaries included in a tomographic image of a fundus of a subject's eye captured by an optical coherence tomography (OCT) optical device;

determining a first region where a density or a luminance of a pixel included in the tomographic image is equal to or greater than a threshold and a second region where a density or a luminance of a pixel is less than the threshold by analyzing the tomographic image, the first region including at least a partial region of a region from an internal limiting membrane to a boundary between an external plexiform layer and an external granular layer, the second region including at least a partial region of a region from the boundary to a photoreceptor cell inner segment/outer segment junction;

comparing a thickness of the first region with a thickness of the second region in a depth direction of the tomographic image; and estimating a position of a fovea of the fundus based on a result of the comparison.

27. A non-transitory computer-readable storage medium storing a program that causes a computer to execute:

detecting a plurality of layer boundaries included in a tomographic image of a fundus of a subject's eye captured by an optical coherence tomography (OCT) optical device;

determining a first region where a density or a luminance of a pixel included in the tomographic image is equal to or greater than a threshold and a second region where a density or a luminance of a pixel is less than the threshold by analyzing the tomographic image, the first region including at least a partial region of a region from an internal limiting membrane to a boundary between an external plexiform layer and an external granular layer, the second region including at least a partial region of a region from the boundary to a photoreceptor cell inner segment/outer segment junction;

comparing a thickness of the first region with a thickness of the second region in a depth direction of the tomographic image; and estimating a position of a fovea of the fundus based on a result of the comparison.

28. A system comprising: an optical coherence tomography (OCT) apparatus configured to acquire a tomographic image of a fundus of a subject's eye;

at least one memory that stores at least one program of instructions; and at least one processor that is coupled to the at least one memory and that executes the at least one program of instructions to implement:

a layer boundary detection unit configured to detect a plurality of layer boundaries included in the tomographic image acquired by the optical coherence tomography (OCT) optical device;

a determination unit configured to determine a first region where a density or a luminance of a pixel included in the tomographic image is equal to or greater than a threshold and a second region where a density or a luminance of a pixel is less than the threshold by analyzing the tomographic image, the first region including at least a partial region of a region from an internal limiting membrane to a boundary between an external plexiform layer and an external granular layer, the second region including at least a partial region of a region from the boundary to a photoreceptor cell inner segment/outer segment junction;

a comparison unit configured to compare a thickness of the first region with a thickness of the second region in a depth direction of the tomographic image; and an estimation unit configured to estimate a position of a fovea of the fundus based on a result of the comparison by the comparison unit.

29. An image processing apparatus comprising:

at least one memory that stores at least one program of instructions; and at least one processor that is coupled to the at least one memory and that executes the at least one program of instructions to implement:

a layer boundary detection unit configured to detect a plurality of layer boundaries included in a tomographic image of a fundus of a subject's eye captured by an optical coherence tomography (OCT) optical device;

a determination unit configured to determine a first region where a density or a luminance of a pixel included in the tomographic image is equal to or greater than a threshold and a second region where a density or a luminance of a pixel is less than the threshold by analyzing the tomographic image;

a comparison unit configured to compare a size of the first region with a size of the second region in a depth direction of the tomographic image; and an estimation unit configured to estimate a position of a fovea of the fundus based on a result of the comparison by the comparison unit.

* * * * *

UNITED STATES PATENT AND TRADEMARK OFFICE
CERTIFICATE OF CORRECTION

Page 1 of 1

PATENT NO. : 10,251,548 B2
APPLICATION NO. : 15/405197
DATED : April 9, 2019
INVENTOR(S) : Hiroyuki Sekiguchi, Akihito Uji and Daisuke Kawase It is certified that error appears in the above-identified patent and that said Letters Patent is hereby corrected as shown below:

On the Title Page

After Item (65) "Prior Publication Data
US 2017/0202453 A1 Jul. 20, 2017"

Please insert the following:
--(30)   Foreign Application Priority Data
Jan. 18, 2016 (JP) ................................ 2016-007429--

Signed and Sealed this
Eleventh Day of June, 2019

Andrei Iancu
*Director of the United States Patent and Trademark Office*